(12) United States Patent
Furet et al.

(10) Patent No.: US 7,691,855 B2
(45) Date of Patent: Apr. 6, 2010

(54) PHENYL-[4-(3-PHENYL-1H-PYRAZOL-4-YL)-PYRIMIDIN-2-YL)-AMINE DERIVATIVES

(75) Inventors: Pascal Furet, Thann (FR); Patricia Imbach, Kaiseraugst (CH); Timothy Michael Ramsey, Weston, MA (US); Achim Schlapbach, Lörrach (DE); Dieter Scholz, Vienna (AT); Giorgio Caravatti, Bottmingen (CH)

(73) Assignee: Novartis AG, Basel (CH)

( * ) Notice: Subject to any disclaimer, the term of this patent is extended or adjusted under 35 U.S.C. 154(b) by 510 days.

(21) Appl. No.: 10/520,567

(22) PCT Filed: Jul. 8, 2003

(86) PCT No.: PCT/EP03/07350

§ 371 (c)(1),
(2), (4) Date: Aug. 24, 2005

(87) PCT Pub. No.: WO2004/005282

PCT Pub. Date: Jan. 15, 2004

(65) Prior Publication Data

US 2006/0106027 A1    May 18, 2006

(30) Foreign Application Priority Data

Jul. 9, 2002 (GB) ................. 0215844.2

(51) Int. Cl.
*C07D 403/04* (2006.01)
*A61K 31/505* (2006.01)

(52) U.S. Cl. ............. 514/235.8; 514/252.19; 514/275; 544/122; 544/295; 544/331

(58) Field of Classification Search .......... 544/122, 544/295, 331; 514/235.8, 252.19, 275
See application file for complete search history.

(56) References Cited

U.S. PATENT DOCUMENTS 6,306,883 B1   10/2001   Adams et al. ............... 514/333

FOREIGN PATENT DOCUMENTS

| WO | 95 19358   | 7/1995  |
| WO | 98 52940   | 11/1998 |
| WO | 98 56377   | 12/1998 |
| WO | 00 31063   | 6/2000  |
| WO | 01 12621   | 2/2001  |
| WO | 01 14375   | 3/2001  |
| WO | 01 60816   | 8/2001  |
| WO | 01 62233   | 8/2001  |
| WO | 01 85700   | 11/2001 |
| WO | 02 46184   | 6/2002  |
| WO | 03 049542  | 6/2003  |

OTHER PUBLICATIONS

Yano et al., Medline Abstract (Clinical Cancer Research: An Official Journal of the American Association For Cancer Research, vol. 6, Issue 3, pp. 957-965), Mar. 2000.*
Cressey et al., Medline Abstract (BMC Cancer, vol. 5, p. 128) Oct. 4, 2005.*
Simone, Cecil Textbook of Medicine, 20th Edition, vol. 1, pp. 1004-1010, 1996.*
Traxler, Protein Tyrosine Kinase inhibitors in cancer treatment, Expert Opinion on Therapeutic Patents, 7(6):571-588, 1997.*
Caplus Abstract Accession No. 2000:368337 & WO 00/31063 A1 (G D Searle & Co.) Jun. 2, 2000 (abstract).

* cited by examiner

Primary Examiner—Deepak Rao

(57) ABSTRACT

The invention relates to phenyl-[4-(3-phenyl-1H-pyrazol-4-yl)-pyrimidin-2-yl]-amine derivatives and to processes for the preparation thereof, to pharmaceutical compositions comprising such derivatives and to the use of such derivatives—alone or in combination with one or more other pharmaceutically active compounds—for the preparation of pharmaceutical compositions for the treatment especially of a proliferative disease, such as a tumor.

6 Claims, No Drawings

PHENYL-[4-(3-PHENYL-1H-PYRAZOL-4-YL)-PYRIMIDIN-2-YL)-AMINE DERIVATIVES

This application is a 371 of PCT/EP03/07350 filed Jul. 8, 2003.

The invention relates to phenyl-[4-(3-phenyl-1H-pyrazol-4-yl)-pyrimidin-2-yl]-amine derivatives and to processes for the preparation thereof, to pharmaceutical compositions comprising such derivatives and to the use of such derivatives—alone or in combination with one or more other pharmaceutically active compounds—for the preparation of pharmaceutical compositions for the treatment especially of a proliferative disease, such as a tumour.

The invention relates to phenyl-[4-(3-phenyl-1H-pyrazol-4-yl)-pyrimidin-2-yl]-amine derivatives of formula I

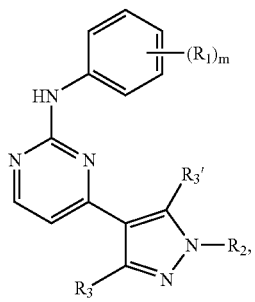

(I)

wherein
m is from 1 to 5;

$R_1$ is lower alkyl-sulfonyl; unsubstituted, mono- or di-substituted amino-sulfonyl; unsubstituted, mono- or di-substituted amino; a heterocyclic radical; lower alkyl substituted by a heterocyclic radical or by heterocyclyl-NH— or heterocyclyl-O— wherein heterocyclyl is bound to NH or O via a carbon ring atom; a radical $R_4$-lower alkyl-X—, wherein $R_4$ is hydrogen, halogen, unsubstituted, mono- or di-substituted amino, or a heterocyclic radical, and X is —S— or —O—; or a radical $R_5$—C(=O)—, wherein $R_5$ is hydrogen, unsubstituted or substituted lower alkyl, free or etherified hydroxy, unsubstituted, mono- or di-substituted amino, or a heterocyclic radical; wherein the $R_1$ substituents are selected independently of one another if m>1;

or two vicinal $R_1$ substituents together with the phenyl carbon atoms to which they are attached form a heterocyclic ring;

$R_2$ is hydrogen, unsubstituted or substituted lower alkyl or a heterocyclic radical;

$R_3$ is hydrogen or a radical of the formula Ia

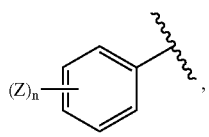

(Ia)

wherein n is from 0 to 5; and
Z is halogen; unsubstituted or substituted lower alkyl; or free, etherified or esterified hydroxy; wherein the Z substituents are selected independently of one another if n>1; or two vicinal Z substituents together with the phenyl carbon atoms to which they are attached form a heterocyclic ring; and $R_3'$ is hydrogen if $R_3$ is a radical of the formula Ia or $R_3'$ is a radical of the formula Ia as defined for $R_3$ if $R_3$ is hydrogen;
with the proviso that $R_1$ is not methoxy if m and n are both 1, $R_2$ is hydrogen and Z is fluoro;

or a salt of the said compounds.

The general terms used hereinbefore and hereinafter preferably have within the context of this disclosure the following meanings, unless otherwise indicated:

Where the plural form is used for compounds, salts, and the like, this is taken to mean also a single compound, salt, or the like.

Asymmetric carbon atoms of a compound of formula I that are optionally present may exist in the (R), (S) or (R,S) configuration, preferably in the (R) or (S) configuration. Substituents at a double bond or a ring may be present in cis- (=Z-) or trans (=E-) form. The compounds may thus be present as mixtures of isomers or preferably as pure isomers.

Preferably alkyl contains up to 20 carbon atoms and is most preferably lower alkyl.

The prefix "lower" denotes a radical having up to and including a maximum of 7, especially up to and including a maximum of 4 carbon atoms, the radicals in question being either unbranched or branched with single or multiple branching.

Lower alkyl is, for example, methyl, ethyl, n-propyl, isopropyl, n-butyl, isobutyl, sec-butyl, tert-butyl, n-pentyl, isopentyl, neopentyl, n-hexyl or n-heptyl.

Lower alkyl $R_2$ is preferably methyl, ethyl or isopropyl, most preferably methyl.

Lower alkyl Z is preferably methyl or ethyl.

Substituted lower alkyl is lower alkyl as defined above where one or more substituents may be present, such as amino, N-lower alkylamino, N,N-di-lower alkylamino, N-lower alkanoylamino, N,N-di-lower alkanoylamino, hydroxy, lower alkoxy, lower alkanoyl, lower alkanoyloxy, cyano, nitro, carboxy, lower alkoxycarbonyl, carbamoyl, amidino, guanidino, ureido, mercapto, lower alkylthio, halogen or a heterocyclic radical.

Substituted lower alkyl $R_2$ is preferably lower alkyl substituted by N,N-di-lower alkylamino or lower alkyl-piperidyl.

Substituted lower alkyl Z is preferably lower alkyl substituted by halogen such as especially trifluoromethyl.

Mono- or di-substituted amino-sulfonyl is amino-sulfonyl, wherein the amino group is substituted by one or two radicals selected independently of one another from e.g. unsubstituted or substituted lower alkyl or a heterocyclic radical.

Unsubstituted, mono- or di-substituted amino-sulfonyl $R_1$ is preferably unsubstituted amino-sulfonyl.

Mono- or di-substituted amino is amino substituted by one or two radicals selected independently of one another from e.g. unsubstituted or substituted lower alkyl or a heterocyclic radical.

Mono- or di-substituted amino $R_1$ is preferably N-lower alkylamino or N,N-di-lower alkylamino, respectively.

Mono- or di-substituted amino $R_4$ is preferably N-lower alkylamino or N,N-di-lower alkylamino, respectively.

$R_4$-lower alkyl-X—, wherein $R_4$ is halogen, includes that the lower alkyl moiety of $R_4$-lower alkyl-X— is substituted with more than one halogen atom, i.e. with up to three halogen atoms, and is preferably trifluoro-lower-alkyl-X.

A heterocyclic radical contains especially up to 20 carbon atoms including possible substituents and is an unsaturated, partially unsaturated, or preferably saturated monocyclic radical having from 4 or 8 ring members and from 1 to 4, especially from 1 to 3, and most preferably 1 or 2 heteroatoms which are preferably selected from nitrogen, oxygen and sulfur, or a bi- or tricyclic radical wherein, for example, one or two benzene radicals are annellated (fused) to the mentioned monocyclic radical. The heterocyclic radical is optionally substituted by one or more radicals such as e.g. unsubstituted or substituted lower alkyl.

In heterocyclyl-NH— and heterocyclyl-O—, the heterocyclyl moiety is as defined for a heterocyclic radical in the preceding paragraph with the proviso that it is bound to NH and O, respectively, via a carbon ring atom and is preferably piperidyl substituted by lower alkyl, such as especially 2,2,6,6-tetramethyl-piperidin-4-yl or 1-methyl-piperidin-4-yl.

A heterocyclic radical $R_1$ is preferably lower alkyl-piperazinyl, especially 4-lower alkyl-piperazin-1-yl.

The heterocyclic ring formed by two vicinal $R_1$ substituents together with the phenyl carbon atoms to which they are attached contains especially up to 20 carbon atoms including possible substituents and is an unsaturated, partially unsaturated, or saturated monocyclic radical having from 4 or 8 ring members and from 1 to 3 heteroatoms which are preferably selected from nitrogen, oxygen and sulfur. The heterocyclic ring is optionally substituted by one or more radicals such as e.g. oxo (=O), thioxo (=S), or unsubstituted or substituted lower alkyl. Preferably this ring is a thiazol, 1-oxo-thiazol or dioxol ring.

Lower alkyl substituted by a heterocyclic radical $R_1$ is preferably lower alkyl substituted by lower alkyl-piperazinyl, especially by 4-lower alkyl-piperazin-1-yl.

A heterocyclic radical $R_4$ is preferably morpholin-4-yl, especially morpholin-4-yl, or lower alkyl-piperidyl, especially 1-lower alkyl-piperidin-4-yl.

A heterocyclic radical $R_5$ is preferably lower alkyl-piperazinyl, especially 4-lower alkyl-piperazin-1-yl.

A heterocyclic radical $R_2$ is preferably bound to the rest of the molecule of formula I via a carbon ring atom and is especially piperidyl, such as piperidin-4-yl, lower alkyl-piperidyl, such as 1-lower alkyl-piperidin-4-yl, or tetrahydro-pyranyl, such as tetrahydro-pyran-4-yl.

Etherified hydroxy is, for example, alkoxy, especially lower alkoxy, such as methoxy, ethoxy and tert-butoxy.

Etherified hydroxy $R_5$ is preferably lower alkoxy, especially ethoxy or tert-butoxy.

Etherified hydroxy Z is preferably lower alkoxy, especially methoxy or ethoxy, or phenyl-lower alkoxy, wherein the phenyl moiety is preferably unsubstituted or substituted by e.g. unsubstituted or substituted lower alkyl.

Esterified hydroxy is preferably hydroxy esterified by an organic carboxylic acid, such as alkanoic acid, and is for example lower alkanoyloxy.

Halogen is primarily fluorine, chlorine, bromine, or iodine, especially fluorine, chlorine, or bromine.

Halogen Z is preferably chloro.

X is preferably —O—.

m is preferably from 1 to 3.

n is preferably 1 or 2.

$R_1$ is preferably attached to the phenyl ring in the meta and/or para position.

Z is preferably attached to the phenyl ring in the meta and/or para position.

$R_4$ is preferably mono- or di-substituted amino, or a heterocylic radical.

Salts are especially the pharmaceutically acceptable salts of compounds of formula I.

Such salts are formed, for example, as acid addition salts, preferably with organic or inorganic acids, from compounds of formula I with a basic nitrogen atom, especially the pharmaceutically acceptable salts.

In the presence of negatively charged radicals, such as carboxy or sulfo, salts may also be formed with bases, e.g. metal or ammonium salts, such as alkali metal or alkaline earth metal salts, or ammonium salts with ammonia or suitable organic amines, such as tertiary monoamines.

In the presence of a basic group and an acid group in the same molecule, a compound of formula I may also form internal salts.

For isolation or purification purposes it is also possible to use pharmaceutically unacceptable salts, for example picrates or perchlorates. Only the pharmaceutically acceptable salts or free compounds (if the occasion arises, in the form of pharmaceutical compositions) attain therapeutic use, and these are therefore preferred.

In view of the close relationship between the novel compounds in free form and in the form of their salts, including those salts that can be used as intermediates, for example in the purification or identification of the novel compounds, hereinbefore and hereinafter any reference to the free compounds is to be understood as referring also to the corresponding salts, as appropriate and expedient.

The compounds of formula I have valuable, pharmacologically useful properties. In particular they are useful for the treatment of proliferative disorders such as especially solid cancers like for example non-small cell lung cancer, squameous carcinoma (head and neck), breast, gastric, ovarian, colon and prostate cancers and gliomas, as well as leukemias, such as especially acute myeloid leukemia (AML) and chronic myeloid leukemia (CML).

The compounds of formula I are effective especially as protein tyrosine kinase inhibitors and/or (furthermore) as inhibitors of serine/threonine protein kinases; they exhibit, for example, powerful inhibition of the tyrosine kinase activity of the epidermal growth factor receptor (EGF-R) and of ErbB-2 kinase. These two protein tyrosine kinase receptors, together with their family members ErbB-3 and ErbB-4, play a key role in signal transmission in a large number of mammalian cells, including human cells, especially epithelial cells, cells of the immune system and cells of the central and peripheral nervous system. For example, in various cell types, EGF-induced activation of receptor-associated protein tyrosine kinase is a prerequisite for cell division and hence for the proliferation of the cell population. Most importantly, overexpression of the EGF-R (HER-1) and/or ErbB2 (HER-2) has been observed in substantial fractions of many human tumours. EGF-R, e.g., was found to be overexpressed in non-small cell lung cancers, squameous carcinoma (head and neck), breast, gastric, ovarian, colon and prostate cancers as well as in gliomas. ErbB2 was found to be overexpressed in squameous carcinoma (head and neck), breast, gastric, and ovarian cancers as well as in gliomas.

In addition to inhibiting the tyrosine kinase activity of the EGF-R, the compounds of formula I also inhibit to varying extents other protein tyrosine kinases that are involved in signal transmission mediated by trophic factors, specially the vascular endothelial growth factor (VEGF) receptor family (e.g. KDR, Flt-1) but also abl kinase, especially v-abl, Flt-3, kinases from the family of Src, especially c-Src, Lck and Fyn, the other members of the EGF receptor family such as ErbB3 (HER-3) and ErbB4 (HER4), CSF-1 receptor, c-Kit, FGF receptor and the cyclin-dependent kinases CDK1 and CDK2, all of which play a part in growth regulation and transformation in mammalian cells, including human cells.

The inhibition of EGF-R tyrosine kinase activity can be demonstrated using known methods, for example using the recombinant intracellular domain of the EGF-receptor [EGF-R ICD; see, for example, E. McGlynn et al., Europ. J. Biochem. 207, 265-275 (1992)]. Compared with the control without inhibitor, the compounds of formula I inhibit the enzyme activity by 50% ($IC_{50}$), for example in a concentration of from 0.0005 to 0.5 µM, especially from 0.001 to 0.1 µM.

As well as or instead of inhibiting EGF-R tyrosine kinase activity, the compounds of formula I also inhibit other members of this family of receptors, like ErbB2. The inhibitory activity ($IC_{50}$) is approximately in the range of 0.001 to 0.5 µM. The inhibition of ErbB2 tyrosine kinase (HER-2) can be determined, for example, analogously to the method used for EGF-R protein tyrosine kinase [see C. House et al., Europ. J. Biochem. 140. 363-367 (1984)]. The ErbB-2 kinase can be isolated, and its activity determined, by means of protocols known per se, for example in accordance with T. Akiyama et al., Science 232 1644 (1986).

Surprisingly, the compounds of formula I especially also inhibit the tyrosine kinase activity of the VEGF receptor family very potently. The compounds of the present invention are therefore very effective dual inhibitors of EGF- and VEGF-receptor family members. For inhibition of KDR and Flt-1 and inhibition of growth factor-induced proliferation of HUVECS see J. Wood et al., Cancer Res. 60, 2178-2189 (2000). The compounds of formula I inhibit e.g. the KDR tyrosine kinase activity with an $IC_{50}$ of from about 1 nM to about 1 µM, especially from about 5 nM to about 0.5 µM.

The action of the compounds of formula I on EGF-induced phosphorylation of the EGF-R can be determined in the human A431 epithelial carcinoma cell line by means of an ELISA which is described in U. Trinks et al., J. Med. Chem. 37:7, 1015-1027 (1994). In that test (EGF-R ELISA) the compounds of formula I exhibit an $IC_{50}$ of approximately from 0.001 to 1 µM.

The compounds of formula I potently inhibit the growth of EGF-R overexpressing NCl-H596 non-small cell lung carcinoma cells [see e.g. W. Lei, et al., Anticancer Res. 19(1A), 221-228 (1999)] at an $IC_{50}$ of approximately 0.01 to 1 µM. In the same range of activity, the compounds of formula I also potently inhibit the growth of ErbB-2-overexpressing BT474 human breast cancer cells. The test procedures are adapted from T. Meyer et al., Int. J. Cancer 43, 851 (1989). The inhibitory activity of the compounds of formula I is determined, briefly, as follows: NCl-H596 cells (10 000/microtitre plate well) are transferred to 96-well microtitre plates. The test compounds [dissolved in dimethyl sulfoxide (DMSO)] are added in a series of concentrations (dilution series) in such a manner that the final concentration of DMSO is not greater than 1% (v/v). After the addition, the plates are incubated for three days during which the control cultures without test compound are able to undergo at least three cell-division cycles. The growth of the NCl-H596 cells is measured by means of methylene blue staining: after the incubation the cells are fixed with glutaraldehyde, washed with water and stained with 0.05% methylene blue. After a washing step the stain is eluted with 3% HCl and the optical density (OD) per well of the microtitre plate is measured using a Titertek Multiskan (Titertek, Huntsville, Ala., USA) at 665 nm. $IC_{50}$ values are determined by a computer-aided system using the formula:

$$IC_{50}=[(OD_{test}-OD_{start})/(OD_{control}-OD_{start})]\times 100.$$

The $IC_{50}$ value in those experiments is given as that concentration of the test compound in question that results in a cell count that is 50% lower than that obtained using the control without inhibitor. The compounds of formula I exhibit inhibitory activity with an $IC_{50}$ in the range from approximately 0.01 to 1 µM.

The compounds of formula I exhibit inhibition of the growth of tumour cells also in vivo, as shown, for example, by the test described below: the test is based on inhibition of the growth of the human squamous lung carcinoma cell line NCl-H596 [ATCC HTB 178; American Type Culture Collection, Rockville, Md., USA; see Santon, J. B., et al., Cancer Research 46, 4701-4705 (1986) and Ozawa, S., et al., Int. J. Cancer 40, 706-710 (1987)], which is transplanted into female BALB/c nude mice (Bomholtgard, Denmark). That carcinoma exhibits a growth that correlates with the extent of the expression of the EGF-R. Tumours are established after subcutaneous (s.c.) injection of cells [a minimum of $2\times 10^6$ cells in 100 µl phosphate-buffered saline (PBS) or medium] in carrier mice (4-8 mice). Injections are made s.c. in the left flank of the mouse mid-way between the tail and the head. The resulting tumours are serially passaged for a minimum of three consecutive transplantations prior to start of the treatment. During this time tumour growth rates stabilize. Tumours are not passaged more than 12 times. For the therapy experiment tumour fragments of roughly 25 mg are transplanted s.c. into the left flank of the animals using a 13-gauge trocar needle under Forene® (Abbott, Schwitzerland) anesthesia. Tumour growth and body weights are monitored twice per week. All treatments are initiated when the tumour attains a volume of 100 to 250 mm³. The tumour volumes are calculated using the known formula Length×Diameter²×π/6 [see Evans, B. D., et al., Brit. J. Cancer 45, 466-8 (1982)]. Antitumour activity is expressed as T/C % (mean increase of tumour volumes of treated animals divided by the mean increase of tumour volumes of control animals multiplied by 100%). At a dose of from 3 to 100 mg/kg of active ingredient, distinct inhibition of the tumour growth is found, for example T/C % values of less than 50.

The compounds of formula I may inhibit other protein tyrosine kinases that are involved in signal transmission mediated by trophic factors, for example abl kinase, such as especially v-abl kinase ($IC_{50}$ for example from 0.01 to 5 µM), kinases from the family of the src kinases, such as especially c-src kinase ($IC_{50}$ for example from 0.1 to 10 µM) and serine/threonine kinases, for example protein kinase C, especially A-Raf, B-Raf and c-Raf and subfamilies thereof, all of these kinases being involved in growth regulation and transformation in mammalian cells, including human cells.

The above-mentioned inhibition of v-abl tyrosine kinase is determined by the methods of N. Lydon et al., Oncogene Research 5, 161-173 (1990) and J. F. Geissler et al., Cancer Research 52, 4492-4498 (1992). In those methods [Val⁵]-angiotensin II and [β-³²P]-ATP are used as substrates.

The compounds of formula I which inhibit the tyrosine kinase activity of the EGF-R or of the other protein tyrosine kinases mentioned are therefore useful, for example, in the treatment of benign or malignant tumours. The compounds of formula I are e.g. able to simultaneously inhibit the growth of tumours with deregulated EGF-R and/or ErbB-2 activity as well as to inhibit the vascularisation of solid tumours triggered by VEGF. This combined activity leads to an improved antitumour effect (see also WO 02/41882). Moreover, the use of a dual inhibitor reduces the risk of drug-drug interactions and further reduces the total drug load as compared to a combination therapy. The compounds of formula I are capable of slowing down tumour growth or effecting tumour regression and of preventing the formation of tumour metastases and the growth of micrometastases. They can be used especially in the case of epidermal hyperproliferation (psoriasis), in the treatment of solid cancers like for example non-small cell lung cancer, squameous carcinoma (head and neck), breast, gastric, ovarian, colon and prostate cancers as well as gliomas and in the treatment of leukemias, such as especially acute myeloid leukemia (AML) and chronic myeloid leukemia (CML). In addition, the compounds of formula I can be used in the treatment of those disorders of the immune system in which several or, especially, individual protein tyrosine kinases and/or (furthermore) serine/threonine protein kinases are involved; the compounds of formula I can also be used in the treatment of those disorders of the central or peripheral nervous system in which signal transmission by several or, especially, a single protein tyrosine kinase(s) and/or (furthermore) serine/threonine protein kinase(s) is/are involved.

In general, the present invention relates also to the use of the compounds of formula I for the inhibition of the mentioned protein kinases, in particular to their use for the dual inhibition of EGF- and VEGF-receptor family members.

The compounds according to the invention can be used both alone and in combination with other pharmacologically active compounds, for example together with inhibitors of the enzymes of polyamine synthesis, inhibitors of protein kinase C, inhibitors of other tyrosine kinases, cytokines, negative growth regulators, for example TGF-β or IFN-β, aromatase inhibitors, antioestrogens and/or cytostatic drugs.

With the groups of preferred compounds of formula I mentioned hereinafter, definitions of substituents from the general definitions mentioned hereinbefore may reasonably be used, for example, to replace more general definitions with more specific definitions or especially with definitions characterized as being preferred.

Preference is given to a compound of formula I, wherein m is an integer from 1 to 5;

$R_1$ is unsubstituted, mono- or di-substituted amino-sulfonyl; unsubstituted, mono- or di-substituted amino; a heterocylic radical; lower alkyl substituted by a heterocyclic radical; a radical $R_4$lower alkyl-X—, wherein $R_4$ is hydrogen, unsubstituted, mono- or di-substituted amino, or a heterocyclic radical, and X is —S— or —O—; or a radical $R_5$—C(=O)—, wherein $R_5$ is hydrogen, unsubstituted or substituted lower alkyl, free or etherified hydroxy, unsubstituted, mono- or di-substituted amino, or a heterocyclic radical; wherein the $R_1$ substituents are selected independently of one another if m>1;

or two vicinal $R_1$ substituents together with the phenyl carbon atoms to which they are attached form a heterocylic ring;

$R_2$ is hydrogen, unsubstituted or substituted lower alkyl or a heterocyclic radical;

$R_3$ is a radical of the formula Ia, wherein n is from 1 to 5 and Z is halogen; unsubstituted or substituted lower alkyl; or free, etherified or esterified hydroxy; wherein the Z substituents are selected independently of one another if n>1;

or two vicinal Z substituents together with the phenyl carbon atoms to which they are attached form a heterocyclic ring; and $R_3'$ is hydrogen;

with the proviso that $R_1$ is not methoxy if m and n are both 1, $R_2$ is hydrogen and Z is fluoro;

and the salts thereof.

Preference is further also given to a compound of formula I, wherein m is an integer from 1 to 5;

$R_1$ is unsubstituted, mono- or di-substituted amino-sulfonyl; unsubstituted, mono- or di-substituted amino; a heterocyclic radical; lower alkyl substituted by a heterocyclic radical; a radical $R_4$-lower alkyl-X—, wherein $R_4$ is hydrogen, unsubstituted, mono- or di-substituted amino, or a heterocyclic radical, and X is —S— or —O—; or a radical $R_5$—C(=O)—, wherein $R_5$ is hydrogen, unsubstituted or substituted lower alkyl, free or etherified hydroxy, unsubstituted, mono- or di-substituted amino, or a heterocyclic radical; wherein the $R_1$ substituents are selected independently of one another if m>1;

or two vicinal $R_1$ substituents together with the phenyl carbon atoms to which they are attached form a heterocyclic ring;

$R_2$ is hydrogen;

$R_3$ is a radical of the formula Ia, wherein n is from 1 to 5 and Z is halogen; unsubstituted or substituted lower alkyl; or free, etherified or esterified hydroxy; wherein the Z substituents are selected independently of one another if n>1;

or two vicinal Z substituents together with the phenyl carbon atoms to which they are attached form a heterocyclic ring; and $R_3'$ is hydrogen;

with the proviso that $R_1$ is not methoxy if m and n are both 1, $R_2$ is hydrogen and Z is fluoro;

and the salts thereof.

Special preference is given to a compound of formula I, wherein m is an integer from 1 to 3;

$R_1$ is amino-sulfonyl; mono- or di-substituted amino; a heterocyclic radical; lower alkyl substituted by a heterocyclic radical; a radical $R_4$ lower alkyl-X—, wherein $R_4$ is hydrogen, mono- or di-substituted amino, or a heterocyclic radical, and X is —S— or —O—; or a radical $R_5$—C(=O)—, wherein $R_5$ is lower alkyl, free or etherified hydroxy, or a heterocyclic radical;

wherein the $R_1$ substituents are selected independently of one another if m>1;

or two vicinal $R_1$ substituents together with the phenyl carbon atoms to which they are attached form a heterocyclic ring;

$R_2$ is hydrogen;

$R_3$ is a radical of the formula Ia, wherein n is from 1 to 3 and Z is halogen; lower alkyl; or free or etherified hydroxy; wherein the Z substituents are selected independently of one another if n>1;

or two vicinal Z substituents together with the phenyl carbon atoms to which they are attached form a heterocyclic ring; and $R_3'$ is hydrogen;

with the proviso that $R_1$ is not methoxy if m and n are both 1, $R_2$ is hydrogen and Z is fluoro;

and the salts thereof.

Very special preference is given to a compound of formula I, wherein m is an integer from 1 to 3;

$R_1$ is lower alkyl-sulfonyl; amino-sulfonyl; N,N-di-lower alkylamino; piperazinyl; lower alkyl-piperazinyl; tetrazolyl; lower alkyl substituted by lower alkyl-piperazinyl, hydroxy-lower alkyl-piperazinyl, piperidyl-amino or piperidyl-oxy wherein the piperidyl moiety is substituted by 1 to 4 lower alkyl radicals; a radical $R_4$-lower alkyl-X—, wherein $R_4$ is hydrogen, halogen, N,N-di-lower alkylamino, morpholinyl or lower alkyl-piperidyl, and X is —S— or —O—; or a radical $R_5$—C(=O)—, wherein $R_5$ is lower alkyl, hydroxy, lower alkoxy or lower alkyl-piperazinyl; wherein the $R_1$ substituents are selected independently of one another if m>1;

or two vicinal $R_1$ substituents together with the phenyl carbon atoms to which they are attached form a thiazol or 1-oxo-thiazol ring;

$R_2$ is hydrogen lower alkyl, N,N-di-lower alkylamino-lower alkyl, lower alkyl-piperidyl or lower alkyl-piperidyl-lower alkyl;

$R_3$ is a radical of the formula Ia, wherein n is 0, 1 or 2 and Z is halogen, lower alkyl, tri-halogen-lower alkyl, hydroxy, lower alkoxy or phenyl-lower alkoxy; wherein the Z substituents are selected independently of one another if n is 2;

or two Z radicals together form a dioxol ring; and $R_3'$ is hydrogen;

with the proviso that $R_1$ is not methoxy if m and n are both 1, $R_2$ is hydrogen and Z is fluoro;

and the salts thereof.

Very special preference is further given to a compound of formula I, wherein m is an integer from 1 to 3;

$R_1$ is amino-sulfonyl; N,N-di-lower alkylamino; lower alkyl-piperazinyl; lower alkyl substituted by lower alkyl-piperazinyl; a radical $R_4$-lower alkyl-X—, wherein $R_4$ is hydrogen, N,N-di-lower alkylamino, morpholinyl or lower alkyl-piperidyl, and X is —S— or —O—; or a radical $R_5$—C(=O)—, wherein $R_5$ is lower alkyl, hydroxy, lower alkoxy or lower alkyl-piperazinyl; wherein the $R_1$ substituents are selected independently of one another if m>1;

or two vicinal $R_1$ substituents together with the phenyl carbon atoms to which they are attached form a thiazol or 1-oxo-thiazol ring;

$R_2$ is hydrogen;

$R_3$ is a radical of the formula Ia, wherein n is 1 or 2 and Z is halogen, lower alkyl, hydroxy, lower alkoxy or phenyl-lower alkoxy; wherein the Z substituents are selected independently of one another if n is 2;

or two Z radicals together form a dioxol ring; and $R_3'$ is hydrogen;

with the proviso that $R_1$ is not methoxy if m and n are both 1, $R_2$ is hydrogen and Z is fluoro;

and the salts thereof.

Very special preference is also given to a compound of formula I, wherein m, $R_1$, $R_2$, $R_3$ and $R_3'$ have the meanings as defined for a compound of formula I, especially as defined for the preferred compounds of formula I, with the proviso that $R_1$ is not a radical $R_4$-lower alkyl-X—, and to salts of such compounds.

Very special preference is further given to a compound of formula I, wherein m is 1 or 2;

$R_1$ is amino-sulfonyl; N,N-di-lower alkylamino; lower alkyl-piperazinyl; lower alkyl substituted by lower alkyl-piperazinyl; or a radical $R_5$—C(=O)—, wherein $R_5$ is lower alkyl, hydroxy, lower alkoxy or lower alkyl-piperazinyl; wherein the $R_1$ substituents are selected independently of one another if m is 2;

or two vicinal $R_1$ substituents together with the phenyl carbon atoms to which they are attached form a thiazol or 1-oxo-thiazol ring;

$R_2$ is hydrogen;

$R_3$ is a radical of the formula Ia, wherein n is 1 or 2 and Z is halogen, lower alkyl, hydroxy, or lower alkoxy; wherein the Z substituents are selected independently of one another if n is 2; and $R_3'$ is hydrogen;

and the salts thereof.

Very special preference is also given to a compound of formula I, wherein $R_1$ is a heterocyclic radical or lower alkyl substituted by a heterocyclic radical, and the salts thereof.

Very special preference is further also given to a compound of formula I, wherein $(R_1)_m$, $R_2$, $R_3$ and $R_3'$ are selected independently of one another from the different meanings given for these substituents in the Examples below, or a salt, especially a pharmaceutically acceptable salt, of such a compound.

Most special preference is given to a compound of formula I mentioned in the Examples below, or a salt, especially a pharmaceutically acceptable salt, thereof.

Also especially preferred are compounds of formula I, which—according to the above-described tyrosine kinase inhibition assays—inhibit HER-1, HER-2 and KDR with $IC_{50}$ values of less than 300 nM, most preferably of less than 100 nM.

Very special preference is further given to compounds of formula I which inhibit the tyrosine kinase activity of at least one member of the EGF receptor family together with at least one member of the VEGF receptor family (dual inhibition of EGF- and VEGF-receptor family members) with $IC_{50}$ values In the range of 0.5 nM to 0.5 µM, especially in the range of 1 nM to 300 nM, based on the above-described tyrosine kinase inhibition assays.

The compounds of formula I or salts thereof are prepared in accordance with processes known per se, though not previously described for the manufacture of the compounds of the formula I, especially whereby a) a compound of formula II

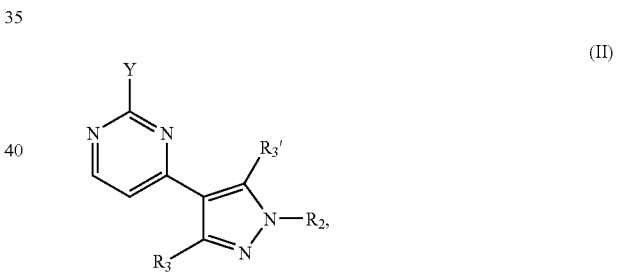

(II)

wherein Y is a leaving group such as halogen, —(=O)—$CH_3$ or —$S(O_2)$—$CH_3$ and $R_2$, $R_3$ and $R_3'$ have the meanings as defined for a compound of formula I, is reacted with a compound of formula III

(III)

wherein m and $R_1$ have the meanings as defined for a compound of formula I;

b) in order to prepare a compound of formula I, wherein $R_1$ is a radical $R_5$—C(=O)— in which $R_5$ is mono- or di-substituted amino or a heterocyclic radical that is bound to the carbonyl moiety via a nitrogen ring atom, a compound of formula IV

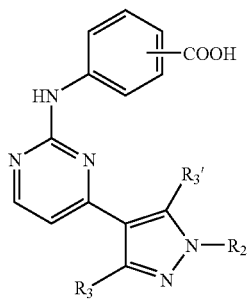

(IV)

wherein $R_2$, $R_3$ and $R_3'$ have the meanings as defined for a compound of formula I, or a reactive carboxylic acid derivative thereof, is reacted with a mono- or di-substituted amine or a heterocyclic radical containing at least one nitrogen ring atom to which a hydrogen is bound, respectively; or c) in order to prepare a compound of formula I, wherein $R_2$ is unsubstituted or substituted lower alkyl or a heterocyclic radical, a compound of formula I, wherein $R_2$ is hydrogen, is reacted with a compound of the formula $R_2$—OH, wherein $R_2$ is unsubstituted or substituted lower alkyl or a heterocyclic radical wherein the substituted lower alkyl or the heterocyclic radical is attached to the hydroxy group of $R_2$—OH via a carbon atom of the lower alkyl moiety or via a carbon ring atom of the heterocyclic radical, respectively;

whereby functional groups which are present in the starting compounds of processes a) to c) and are not intended to take part In the reaction, are present in protected form if necessary, and protecting groups that are present are cleaved, whereby the said starting compounds may also exist in the form of salts provided that a salt-forming group is present and a reaction in salt form is possible;

and, if so desired, a compound of formula I thus obtained is converted into another compound of formula I, a free compound of formula I is converted into a salt, an obtained salt of a compound of formula I is converted into the free compound or another salt, and/or a mixture of isomeric compounds of formula I is separated into the individual isomers.

Description of the Process Variants:

Regarding Process a):

The reaction between a compound of formula II, wherein Y is halogen, and a compound of formula III preferably takes place in a suitable inert solvent such as dioxane, in the presence of an acid such as HCl, at elevated temperature, preferably at around 100° C. In a compound of formula II wherein Y is halogen, halogen is preferably chloro or bromo, especially chloro.

The reaction between a compound of formula II, wherein Y is —S($O_2$)—$CH_3$, and a compound of formula III preferably takes place under those conditions described for the analogous procedure in Klutchko et al., Journal of Medicinal Chemistry, 1998, Vol. 41, No. 17, 3276-3292.

The reaction between a compound of formula II, wherein Y is —S(=O)—$CH_3$, and a compound of formula III preferably takes place in a suitable inert solvent such as 1,4-dioxane or tetrahydrofuran, in the presence of $BF_3.Et_2O$, at elevated temperature, preferably at around 100° C.

Regarding Process b):

Reaction b), that is, the formation of amide bonds, preferably takes place under standard conditions for the formation of peptide bonds (condensation reaction). In a reactive carboxylic acid derivative of a compound of the formula IV, the carboxyl group is either functionalized as activated ester (reactive form). The reactive carboxyl groups are, however, preferably synthesized in situ (for example making use of reagents customary in peptide chemistry, e.g. for the preparation of 1-hydroxybenzotriazole, succinimide- or N-hydroxysuccinimide esters, or in situ derivatisation with condensing agents, e.g. with carbodiimides, such as dicyclohexylcarbodiimide, with carbonylimidazole, with N-[(dimethylamino)-1H-1,2,3-triazolo[4,5-b]pyridin-1-ylmethylene]-N-methyl-methanaminiumhexafluorophosphate-N-oxide (HATU); with 2-(1H-benzotriazol-1-yl)-1,1,3,3-tetramethyluroniumtetrafluoroborat (HBTU), with 2-(pyridon-1-yl)-1,1,3,3-tetramethyluroniumtetrafluoroborate (TPTU); or benzotriazol-1-yl-oxy-tris(dimethylamino) phosphoniumhexafluorophosphate (BOP), or similar reagents). The condensation reaction preferably takes place in the presence of a condensing agent, especially BOP, in an aprotic polar solvent, preferably a N,N-di-(lower alkyl)-lower alkanoylamide, such as dimethylformamide, at preferred temperatures in the range from 0 to 50° C., e.g. at room temperature.

Regarding Process c):

The reaction between a compound of formula I, wherein $R_2$ is hydrogen, and a compound of the formula $R_2$—OH preferably takes place under the Mitsunobu reaction conditions such as those described in: Mitsunobu, Oyo; Synthesis 1981, p. 1-27.

Compounds of formula I can be transformed into different compounds of formula I. Such transformations include: reduction of a carbonyl group to a methylene group as in Example 32; ether cleavage as in Example 39; oxidation of a sulfide to a sulfoxide as in Example 45; de-chlorination as in Example 104; alkylation as in Example 117.

Additonal Process Steps:

In the additional process steps, carried out as desired, functional groups of the starting compounds which should not take part in the reaction may be present in unprotected form or may be protected for example by one or more protecting groups. The protecting groups are then wholly or partly removed according to one of the known methods.

Protecting groups, and the manner in which they are introduced and removed are described, for example, in "Protective Groups in Organic Chemistry", Plenum Press, London, N.Y. 1973, and in "Methoden der organischen Chemie", Houben-Weyl, 4th edition, Vol. 15/1, Georg-Thieme-Verlag, Stuttgart 1974 and in Theodora W. Greene, "Protective Groups in Organic Synthesis", John Wiley & Sons, New York 1981. A characteristic of protecting groups is that they can be removed readily, i.e. without the occurrence of undesired secondary reactions, for example by solvolysis, reduction, photolysis or alternatively under physiological conditions.

The end products of formula I may however also contain substituents that can also be used as protecting groups in starting materials for the preparation of other end products of formula I. Thus, within the scope of this text, only a readily removable group that is not a constituent of the particular desired end product of formula I is designated a "protecting group", unless the context indicates otherwise.

General Process Conditions:

All process steps described here can be carried out under known reaction conditions, preferably under those specifically mentioned, in the absence of or usually in the presence of solvents or diluents, preferably those that are Inert to the reagents used and able to dissolve them, in the absence or presence of catalysts, condensing agents or neutralising agents, for example ion exchangers, typically cation exchangers, for example in the H⁺ form, depending on the type of reaction and/or reactants at reduced, normal, or elevated temperature, for example in the range from −100° C. to about 190° C., preferably from about −80° C. to about 150° C., for example at −80 to −60° C., at RT, at −20 to 40° C., at 0 to 100° C. or at the boiling point of the solvent used, under atmospheric pressure or in a closed vessel, if need be under pressure, and/or in an inert, for example an argon or nitrogen, atmosphere.

The invention relates also to those embodiments of the process in which one starts from a compound obtainable at any stage as an intermediate and carries out the missing steps, or breaks off the process at any stage, or forms a starting material under the reaction conditions, or uses said starting material in the form of a reactive derivative or salt, or produces a compound obtainable by means of the process according to the invention under those process conditions, and further processes the said compound in situ. In the preferred embodiment, one starts from those starting materials which lead to the compounds described hereinabove as preferred.

In the preferred embodiment, a compound of formula I is prepared according to the processes and process steps defined in the Examples.

The compounds of formula I, including their salts, are also obtainable in the form of hydrates, or their crystals can include for example the solvent used for crystallisation (present as solvates).

Starting Materials:

New starting materials and/or intermediates, as well as processes for the preparation thereof, are likewise the subject of this invention. In the preferred embodiment, such starting materials are used and reaction conditions so selected as to enable the preferred compounds to be obtained.

The starting materials used in the above described processes a) to c) are known, capable of being prepared according to known processes, or commercially obtainable; in particular, they can be prepared using processes as described In the Examples.

In the preparation of starting materials, existing functional groups which do not participate in the reaction should, if necessary, be protected. Preferred protecting groups, their introduction and their removal are described above or in the Examples. In place of the respective starting materials and transients, salts thereof may also be used for the reaction, provided that salt-forming groups are present and the reaction with a salt is also possible. Where the term starting materials is used hereinbefore and hereinafter, the salts thereof are always included, insofar as reasonable and possible.

A compound of formula II, wherein Y is halogen, $R_2$ is hydrogen or lower alkyl, and $R_3$ and $R_3'$ have the meanings as defined for a compound of formula I, can be prepared for example by reacting a compound of formula V

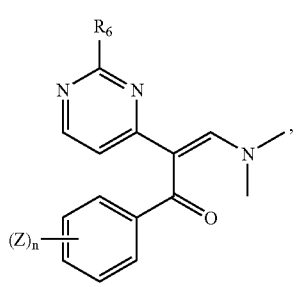

(V)

wherein $R_6$ is halogen and n and Z have the meanings as defined for a compound of formula I with hydrazine ($H_2N$—$NH_2$) or N-lower alkyl-hydrazine (lower alkyl-NH—$NH_2$), respectively, in a suitable solvent, e.g. lower alcohols, such as ethanol, preferably at around room temperature.

A compound of the formula II, wherein Y is halogen, $R_2$ is unsubstituted or substituted lower alkyl or a heterocyclic radical, and $R_3$ and $R_3'$ have the meanings as defined for a compound of formula I, can be prepared for example by reacting a compound of formula II, wherein Y is halogen, $R_2$ is hydrogen and $R_3$ and $R_3'$ have the meanings as defined for a compound of formula I, with a compound of the formula $R_2$—OH, wherein $R_2$ is unsubstituted or substituted lower alkyl or a heterocyclic radical wherein the substituted lower alkyl or the heterocyclic radical is attached to the hydroxy group of $R_2$—OH via a carbon atom of the lower alkyl moiety or via a carbon ring atom of the heterocyclic radical, respectively, e.g. under the Mitsunobu reaction conditions such as those described in: Mitsunobu, Oyo; Synthesis 1981, p. 1-27.

A compound of formula II, wherein Y is —$S(O_2)$—$CH_3$ and $R_2$, $R_3$ and $R_3'$ have the meanings as defined for a compound of formula I, can be prepared for example by reacting a compound of formula VI

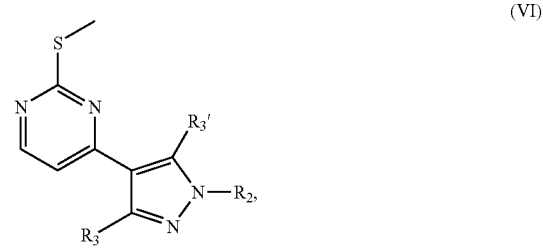

(VI)

wherein $R_2$, $R_3$ and $R_3'$ have the meanings as defined for a compound of formula I, with 3-chloroperoxybenzoic acid in $CHCl_3$, e.g. under those conditions described for the analogous procedure in Klutchko et al., Journal of Medicinal Chemistry, 1998, Vol. 41, No. 17, 3276-3292.

A compound of formula II, wherein Y is —S(=O)—$CH_3$ and $R_2$, $R_3$ and $R_3'$ have the meanings as defined for a compound of formula I, can be prepared for example by reacting a compound of formula VI with 3-chloroperoxybenzoic acid under conditions such as those described in M. P. Zawistoski, *Journal of Heterocyclic Chemistry*, 1991, Volume 28, p. 657-665.

A compound of formula IV, or a reactive carboxylic acid derivative thereof, wherein $R_2$, $R_3$ and $R_3'$ have the meanings as defined for a compound of formula I, can be prepared for example by reacting a compound of formula II, wherein Y is a leaving group such as halogen, —S(=O)—$CH_3$ or —$S(O_2)$—$CH_3$ and $R_2$, $R_3$ and $R_3'$ have the meanings as defined for a compound of formula I, with amino-benzoic acid, e.g. under conditions described for the reaction of a compound of formula II with a compound of formula III, and activate the carboxy group of benzoic acid thereafter.

A compound of formula VI, wherein $R_2$ is hydrogen or lower alkyl and $R_3$ and $R_3'$ have the meanings as defined for a compound of formula I, can be prepared for example by reacting a compound of formula V, wherein $R_6$ is —S—$CH_3$ and n and Z have the meanings as defined for a compound of formula I, with hydrazine ($H_2N$—$NH_2$) or N-lower alkyl-hydrazine (lower alkyl-NH—NH$_2$), respectively, in a suitable solvent, e.g. lower alcohols, such as ethanol, preferably at around room temperature.

A compound of formula VI, wherein R$_2$ is unsubstituted or substituted lower alkyl or a heterocyclic radical, and R$_3$ and R$_3$' have the meanings as defined for a compound of formula I, can be prepared for example by reacting a compound of formula VI, wherein R$_2$ is hydrogen and R$_3$ and R$_3$' have the meanings as defined for a compound of formula I, with a compound of the formula R$_2$—OH, wherein R$_2$ is unsubstituted or substituted lower alkyl or a heterocyclic radical wherein the substituted lower alkyl or the heterocyclic radical is attached to the hydroxy group of R$_2$—OH via a carbon atom of the lower alkyl moiety or via a carbon ring atom of the heterocyclic radical, respectively, e.g. under the Mitsunobu reaction conditions such as those described in: Mitsunobu, Oyo; Synthesis 1981, p. 1-27.

A compound of formula V, wherein R$_5$ is halogen or —S—CH$_3$ and n and Z have the meanings as defined for a compound of formula I, can be prepared for example by reacting a compound of formula VII

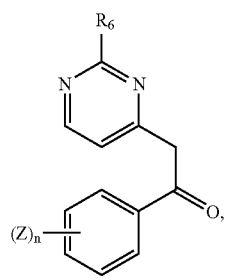

(VII)

wherein R$_6$ is halogen or —S—CH$_3$, respectively, and n and Z have the meanings as defined for a compound of formula I, with N,N-dimethylformamid-dimethylacetal, at elevated temperature, preferably at around 100° C.

A compound of formula VII, wherein R$_6$ is halogen and n and Z have the meanings as defined for a compound of formula I, can be prepared for example by reacting a compound of formula VIII

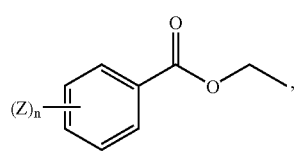

(VIII)

wherein n and Z have the meanings as defined for a compound of formula I, with a compound of formula IX

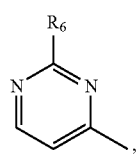

(IX)

wherein R$_6$ is halogen, in the presence of lithiumdiisopropylamide, in a suitable organic solvent or mixture of solvents, preferably starting the reaction at reduced temperature, preferably at around −75° C., and letting it to reach room temperature.

A compound of formula VII, wherein R$_6$ is —S—CH$_3$ and n and Z have the meanings as defined for a compound of formula I, can be prepared for example by reacting a compound of formula X

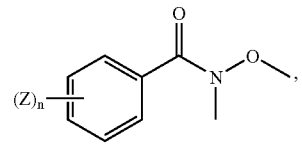

(X)

wherein n and Z have the meanings as defined for a compound of formula I, with a compound of formula IX, wherein R$_6$ is —S—CH$_3$, in the presence of lithiumdiisopropylamide, in a suitable organic solvent or mixture of solvents, preferably starting the reaction at reduced temperature, preferably at around −75° C., and letting it to reach room temperature.

A compound of formula X, wherein n and Z have the meanings as defined for a compound of formula I, can be prepared for example by reacting a compound of formula XI

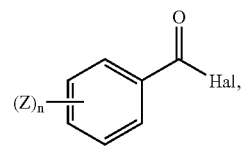

(XI)

wherein Hal is halogen, such as chloro, and n and Z have the meanings as defined for a compound of formula I, with N—O-dimethylhydroxylamine HCl in CH$_2$Cl$_2$, e.g. under those conditions described for the analogous procedure in Nahm, Steven; Weinreb, Steven M.; *Tetrahedron Lett.;* 1981; 22 (39); 3815-3818.

The remaining starting materials are known, capable of being prepared according to known processes, or commercially available; or in particular, they can be prepared using processes as described in the Examples.

Pharmaceutical Compositions, Methods, and Uses:

The present invention relates also to pharmaceutical compositions that comprise a compound of formula I, or a pharmaceutically acceptable salt thereof, as active ingredient and that can be used especially in the treatment of the diseases mentioned at the beginning. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions contain the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The present invention also relates to pro-drugs of a compound of formula I that convert in vivo to the compound of formula I as such. Any reference to a compound of formula I is therefore to be understood as referring also to the corresponding pro-drugs of the compound of formula I, as appropriate and expedient.

The invention relates also to compounds of formula I, or a pharmaceutically acceptable salt thereof, as such or in the form of a pharmaceutical composition, for use in a method for the prophylactic or especially therapeutic treatment of the human or animal body, to a process for the preparation thereof (especially in the form of compositions for the treatment of tumours) and to a method of treating proliferative diseases, primarily tumour diseases, especially those mentioned above.

The invention relates also to processes and to the use of compounds of formula I, or a pharmaceutically acceptable salt thereof, for the preparation of pharmaceutical compositions which comprise compounds of formula I, or a pharmaceutically acceptable salt thereof, as active component (active ingredient).

If desired, the said pharmaceutical compositions may also contain further active components, for example cytostatics, and/or may be used in combination with known therapeutic processes, for example the administration of hormones or radiation.

Preference is given for a pharmaceutical composition which is suitable for administration to a warm-blooded animal, especially humans or commercially useful mammals suffering from a disease which responds to an inhibition of a protein tyrosine kinase, especially to a dual inhibition of EGF- and VEGF-receptor family members, especially a neoplastic disease, comprising an effective quantity of a compound of formula I for the inhibition of a protein tyrosine kinase, especially for the dual inhibition of EGF- and VEGF-receptor family members, or a pharmaceutically acceptable salt thereof, together with at least one pharmaceutically acceptable carrier.

A pharmaceutical composition for the prophylactic or especially therapeutic management of neoplastic and other proliferative diseases of a warm-blooded animal, especially a human or a commercially useful mammal requiring such treatment, especially suffering from such a disease, comprising as active ingredient in a quantity that is prophylactically or especially therapeutically active against said diseases a compound of formula I, or a pharmaceutically acceptable salt thereof, is likewise preferred.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories or capsules. Examples are capsules containing from about 0.05 g to about 1.0 g of active substance.

The pharmaceutical compositions of the present invention are prepared in a manner known per se, for example by means of conventional mixing, granulating, coating, dissolving or lyophilising processes.

The invention relates likewise to a process or a method for the treatment of one of the pathological conditions mentioned hereinabove, especially a disease which responds to an inhibition of a protein tyrosine kinase, especially to a dual inhibition of EGF- and VEGF-receptor family members, especially a corresponding neoplastic disease. The compounds of formula I, or pharmaceutically acceptable salts thereof, can be administered as such or in the form of pharmaceutical compositions, prophylactically or therapeutically, preferably in an amount effective against the said diseases, to a warm-blooded animal, for example a human, requiring such treatment, the compounds especially being used in the form of pharmaceutical compositions. In the case of an individual having a bodyweight of about 70 kg the daily dose administered is from approximately 0.1 g to approximately 5 g, preferably from approximately 0.5 g to approximately 2 g, of a compound of the present invention.

The present invention relates especially also to the use of a compound of formula I, or a pharmaceutically acceptable salt thereof, especially a compound of formula I which is said to be preferred, or a pharmaceutically acceptable salt thereof, as such or in the form of a pharmaceutical composition with at least one pharmaceutically acceptable carrier, for the therapeutic and also prophylactic management of one or more of the diseases mentioned hereinabove, preferably a disease which responds to an inhibition of a protein tyrosine kinase, especially to a dual inhibition of EGF- and VEGF-receptor family members, especially a neoplastic disease, in particular if the said disease responds to an inhibition of a protein tyrosine kinase, especially to a dual inhibition of EGF- and VEGF-receptor family members.

The present invention relates especially also to the use of a compound of formula I, or a pharmaceutically acceptable salt thereof, especially a compound of formula I which is said to be preferred, or a pharmaceutically acceptable salt thereof, for the preparation of a pharmaceutical composition for the therapeutic and also prophylactic management of one or more of the diseases mentioned hereinabove, especially a neoplastic disease, in particular if the disease responds to an inhibition of a protein tyrosine kinase, especially to a dual inhibition of EGF- and VEGF-receptor family members.

A compound of formula I may also be used to advantage in combination with other antiproliferative agents. Such antiproliferative agents include, but are not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, anti-androgens, bengamides, bisphosphonates, antiproliferative antibodies and temozolomide (TEMODAL®).

The term "aromatase inhibitors" as used herein relates to compounds which inhibit the estrogen production, i.e. the conversion of the substrates androstenedione and testosterone to estrone and estradiol, respectively. The term includes, but is not limited to steroids, especially exemestane and formestane and, in particular, non-steroids, especially aminoglutethimide, vorozole, fadrozole, anastrozole and, very especially, letrozole. Exemestane can be administered, e.g., in the form as it is marketed, e.g. under the trademark AROMASIN™. Formestane can be administered, e.g., in the form as it is marketed, e.g. under the trademark LENTARON™. Fadrozole can be administered, e.g., in the form as it is marketed, e.g. under the trademark AFEMA™. Anastrozole can be administered, e.g., in the form as it is marketed, e.g. under the trademark ARIMIDEX™. Letrozole can be administered, e.g., in the form as it is marketed, e.g. under the trademark FEMARA™ or FEMAR™. Aminoglutethimide can be administered, e.g., in the form as it is marketed, e.g. under the trademark ORIMETEN™.

A combination of the invention comprising an antineoplastic agent which is an aromatase inhibitor is particularly useful for the treatment of hormone receptor positive breast tumours.

The term "antiestrogens" as used herein relates to compounds which antagonize the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX™. Raloxifene hydrochloride can be administered, e.g., in the form as it is marketed, e.g. under the trademark EVISTA™. Fulvestrant can be formulated as disclosed in U.S. Pat. No. 4,659,516 or it can be administered, e.g., in the form as it is marketed, e.g. under the trademark FASLODEX™.

The term "topoisomerase I inhibitors" as used herein includes, but is, not limited to topotecan, irinotecan, 9-nitrocamptothecin and the macromolecular camptothecin conjugate PNU-166148 (compound A1 in WO99/17804). Irinotecan can be administered, e.g., in the form as it is marketed, e.g. under the trademark CAMPTOSAR™. Topotecan can be administered, e.g., in the form as it is marketed, e.g. under the trademark HYCAMTIN™.

The term "topoisomerase II inhibitors" as used herein includes, but is not limited to the antracyclines doxorubicin (including liposomal formulation, e.g. CAELYX™), epirubicin, idarubicin and nemorubicin, the anthraquinones mitoxantrone and losoxantrone, and the podophillotoxines etoposide and teniposide. Etoposide can be administered, e.g., in the form as it is marketed, e.g. under the trademark ETOPOPHOS™. Teniposide can be administered, e.g., in the form as H is marketed, e.g. under the trademark VM 26BRISTOL™. Doxorubicin can be administered, e.g., in the form as it is marketed, e.g. under the trademark ADRIBLASTIN™. Epirubicin can be administered, e.g., in the form as it is marketed, e.g. under the trademark FARMORUBICIN™. Idarubicin can be administered; e.g., in the form as it is marketed, e.g. under the trademark ZAVEDOS™. Mitoxantrone can be administered, e.g., in the form as it is marketed, e.g. under the trademark NOVANTRON™.

The term "microtubule active agents" relates to microtubule stabilizing and microtubule destabilizing agents including, but not limited to the taxanes paclitaxel and docetaxel, the vinca alkaloids, e.g., vinblastine, especially vinblastine sulfate, vincristine especially vincristine sulfate, and vinorelbine, discodermolide and epothilones, such as epothilone B and D. Docetaxel can be administered, e.g., in the form as it is marketed, e.g. under the trademark TAXOTERE™. Vinblastine sulfate can be administered, e.g., in the form as it is marketed, e.g. under the trademark VINBLASTIN R.P.™. Vincristine sulfate can be administered, e.g., in the form as it is marketed, e.g. under the trademark FARMISTIN™. Discodermolide can be obtained, e.g., as disclosed in U.S. Pat. No. 5,010,099.

The term "alkylating agents" as used herein includes, but is not limited to cyclophosphamide, ifosfamide and melphalan. Cyclophosphamide can be administered, e.g., in the form as it is marketed, e.g. under the trademark CYCLOSTIN™. Ifosfamide can be administered, e.g., in the form as it is marketed, e.g. under the trademark HOLOXAN™.

The term "histone deacetylase inhibitors" relates to compounds which inhibit the histone deacetylase and which possess antiproliferative activity.

The term "farnesyl transferase inhibitors" relates to compounds which inhibit the farnesyl transferase and which possess antiproliferative activity.

The term "COX-2 inhibitors" relates to compounds which inhibit the cyclooxygenase type 2 enyzme (COX-2) and which possess antiproliferative activity such as celecoxib (Celebrex®), rofecoxib (Vioxx®) and lumiracoxib (COX189).

The term "MMP inhibitors" relates to compounds which inhibit the matrix metalloproteinase (MMP) and which possess antiproliferative activity.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "antineoplastic antimetabolites" includes, but is not limited to 5-fluorouracil, tegafur, capecitabine, cladribine, cytarabine, fludarabine phosphate, fluorouridine, gemcitabine, 6-mercaptopurine, hydroxyurea, methotrexate, edatrexate and salts of such compounds, and furthermore ZD 1694 (RALTITREXED™), LY231514 (ALIMTA™), LY264618 (LOMOTREXOL™) and OGT719.

The term "platin compounds" as used herein includes, but is not limited to carboplatin, cisplatin and oxaliplatin. Carboplatin can be administered, e.g., in the form as it is marketed, e.g. under the trademark CARBOPLAT™. Oxaliplatin can be administered, e.g., in the form as it is marketed, e.g. under the trademark ELOXATIN™.

The term "compounds decreasing the protein kinase activity and further anti-angiogenic compounds" as used herein includes, but is not limited to compounds which decrease the activity of e.g. the Vascular Endothelial Growth Factor (VEGF), the Epidermal Growth Factor (EGF), c-Src, protein kinase C, Platelet-derived Growth Factor (PDGF), Bcr-Abl tyrosine kinase, c-kit, Flt-3 and insulin-like Growth Factor I Receptor (IGF-IR) and Cyclin-dependent kinases (CDKs), and anti-angiogenic compounds having another mechanism of action than decreasing the protein kinase activity.

Compounds which decrease the activity of VEGF are especially compounds which inhibit the VEGF receptor, especially the tyrosine kinase activity of the VEGF receptor, and compounds binding to VEGF, and are in particular those compounds, proteins and monoclonal antibodies generically and specifically disclosed in WO 98/35958 (describing compounds of formula I), WO 00/09495, WO 00/27820, WO 00/59509, WO 98/11223, WO 00/27819, WO 01155114, WO 01/58899 and EP 0 769 947; those as described by M. Prewett et al in Cancer Research 59 (1999) 5209-5218, by F. Yuan et al in Proc. Natl. Acad. Sci. USA, vol. 93, pp. 14765-14770, December 1996, by Z. Zhu et al in Cancer Res. 58, 1998, 3209-3214, and by J. Mordenti et al in Toxicologic Pathology, vol. 27, no. 1, pp 14-21, 1999; in WO 00/37502 and WO 94/10202; Angiostatin™, described by M. S. O'Reilly et al, Cell 79, 1994, 315-328; and Endostatin™, described by M. S. O'Reilly et al, Cell 88, 1997, 277-285; compounds which decrease the activity of EGF are especially compounds which inhibit the EGF receptor, especially the tyrosine kinase activity of the EGF receptor, and compounds binding to EGF, and are in particular those compounds generically and specifically disclosed in WO 97/02266 (describing compounds of formula IV), EP 0 564 409, WO 99/03854, EP 0520722, EP 0 566 226, EP 0 787 722, EP 0 837 063, WO 98/10767, WO 97/30034, WO 97/49688, WO 97/38983 and, especially, WO 96/33980; compounds which decrease the activity of c-Src include, but are not limited to, compounds inhibiting the c-Src protein tyrosine kinase activity as defined below and to SH2 interaction inhibitors such as those disclosed in WO97/07131 and WO97/08193; compounds inhibiting the c-Src protein tyrosine kinase activity include, but are not limited to, compounds belonging to the structure classes of pyrrolopyrimidines, especially pyrrolo[2,3-d]pyrimidines, purines, pyrazopyrimidines, especially pyrazo[3,4-d]pyrimidines, pyrazopyrimidines, especially pyrazo[3,4-d]pyrimidines and pyridopyrimidines, especially pyrido[2,3-d]pyrimidines.

Preferably, the term relates to those compounds disclosed in WO 96/10028, WO 97/28161, WO97/32879 and WO97/49706; compounds which decreases the activity of the protein kinase C are especially those staurosporine derivatives disclosed in EP 0 296 110 (pharmaceutical preparation described in WO 00/48571) which compounds are protein kinase C inhibitors; further specific compounds that decrease protein kinase activity and which may also be used in combination with the compounds of the present invention are Imatinib (Gleevec®/Glivec®), PKC412, Iressa™ (ZD1839), PKI166, PTK787, ZD6474, GW2016, CHIR-200131, CEP-7055/CEP-5214, CP-547632 and KRN-633; anti-anglogenic compounds having another mechanism of action than decreasing the protein kinase activity include, but are not limited to e.g. thalidomide (THALOMID), celecoxib (Celebrex), SU5416 and ZD6126.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX™. Abarelix can be formulated, eg. as disclosed in U.S. Pat. No. 5,843,901.

The term "anti-androgens" as used herein includes, but is not limited to bicalutamide (CASODEX™), which can be formulated, e.g. as disclosed in U.S. Pat. No. 4,636,505.

The term "bengamides" relates to bengamides and derivatives thereof having aniproliferative properties.

The term "bisphosphonates" as used herein includes, but is not limited to etridonic acid, clodronic acid, tiludronic acid, pamidronic acid, alendronic acid, ibandronic acid, risedronic acid and zoledronic acid. "Etridonic acid" can be administered, e.g., in the form as it is marketed, e.g. under the trademark DIDRONEL™. "Clodronic acid" can be administered, e.g., in the form as it is marketed, e.g. under the trademark BONEFOS™. "Tiludronic acid" can be administered, e.g., in the form as it is marketed, e.g. under the trademark SKELID™. "Pamidronic acid" can be administered, e.g., in the form as it is marketed, e.g. under the trademark AREDIA™. "Alendronic acid" can be administered, e.g., in the form as it is marketed, e.g. under the trademark FOSAMAX™. "Ibandronic acid" can be administered, e.g., in the form as it is marketed, e.g. under the trademark BONDRANAT™. "Risedronic acid" can be administered, e.g., in the form as it is marketed, e.g. under the trademark ACTONEL™. "Zoledronic acid" can be administered, e.g., in the form as it is marketed, e.g. under the trademark ZOMETA™.

The term "antiproliferative antibodies" as used herein includes, but is not limited to trastuzumab (Herceptin™), Trastuzumab-DM1, erlotinib (Tarceva™), bevacizumab (Avastin™), rituximab (Rituxan®), PRO64553 (anti-CD40) and 2C4 Antibody.

For the treatment of AML, compounds of formula I can be used in combination with standard leukemia therapies, especially in combination with therapies used for the treatment of AML. In particular, compounds of formula I can be administered in combination with e.g. farnesyltransferase inhibitors and for other drugs used for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of formula I, can be prepared and administered as described in the art such as in the documents cited above.

EXAMPLES

The following Examples serve to illustrate the invention without limiting its scope.

Temperatures are measured in degrees Celsius. Unless otherwise indicated, the reactions take place at RT.

The $R_f$ values which indicate the ratio of the distance moved by each substance to the distance moved by the eluent front are determined on silica gel thin-layer plates (Merck, Darmstadt, Germany) by thin-layer chromatography using the respective named solvent systems.

Analytical HPLC Conditions:

System 1:

Linear gradient 20-100% $CH_3CN$ [0.1% trifluoroacetic acid (TFA)] and $H_2O$ (0.1% TFA) in 7 min+2 min 100% $CH_3CN$ (0.1% TFA); detection at 215 nm, flow rate 1 mL/min at 30° C. Column: Nucleosil 100-3 C18HD (125×4 mm).

System 2:

Linear gradient 2-100% $CH_3CN$ (0.1% TFA) and $H_2O$ (0.1% TFA) in 10 min+2 min 100% $CH_3CN$ (0.1% TFA); detection at 216 nm, flow rate 2 mL/min at rt. Column: Nucleosil 100-3 C18HD (125×4 mm).

System 3:

Linear gradient 10→90% $CH_3CN$ in $H_2O$ (0.1% TFA) in 10 min; detection at 215, 230, 254, 280 nm, flow rate 2 mL/min at 20° C. Column: Nova-Pak C18HD (150×3.9 mm).

System 4:

10% $CH_3CN$ in $H_2O$ (0.1% TFA) for 5 min, then linear gradient 10→90% $CH_3CN$ in $H_2O$ (0.1% TFA) in 25 min; detection at 215, 230, 254, 280 nm, flow rate 2 mL/min at 20° C. Column: Nova-Pak C18HD (150×3.9 mm).

System 5:

10% $CH_3CN$/90% $H_2O$ (0.1% TFA) for 1 min, then linear gradient 10→70% $CH_3CN$ in $H_2O$ (0.1% TFA) in 19 min, then hold 70% $CH_3CN$ in $H_2O$ (0.1% TFA) for 15 min; detection at 254 nm, flow rate 1.5 mL/min at 20° C. Column: Nova-Pak C18 (4.6×250 mm).

System XS:

Column: (50×4.6 mm) packed with reversed-phase material C18-Nucleosil (Interchrom UP3ODB-5QS, Optisphere 3 μM ODB). Detection by UV absorption at 215 nm. The retention times ($t_R$) are given in minutes. Flow rate: 2 ml/min.

Gradient: 15%→100% a) in b) for 2.25 min+1.25 min 100% a). a): Acetonitrile+0.1% TFA; b): water+0.1% TFA.

System XI:

Column: (250×4.6 mm) packed with reversed-phase materal C18Nucleosil (5 μm mean particle size, with silica gel covalently derivatized with octadecylsilanes, Macherey & Nagel, Düren, Germany). Detection by UV absorption at 215 nm. The retention times ($t_R$) are given in minutes. Flow rate: 1 ml/min.

Gradient: 20%→100% a) in b) for 14 min+5 min 100% a). a): Acetonitrile+0.1% TFA; b): water+0.1% TFA.

System X2:

Column: (250×4.6 mm) packed with reversed-phase material C18-Nucleosil (5 μm mean particle size, with silica gel covalently derivatized with octadecylsilanes, Macherey & Nagel, Düren, Germany). Detection by UV absorption at 215 nm. The retention times ($t_R$) are given in minutes. Flow rate: 1 ml/min.

Gradient: 5%→40% a) in b) for 9 min+7 min 100% a). a): Acetonitrile+0.1% TFA; b): water+0.1% TFA.

| Abbreviations: | |
|---|---|
| abs. | absolute |
| approx. | approximately |
| aq. | Aqueous |
| BOC | tert-butoxycarbonyl |
| BOP | (benzotriazol-1-yloxy)-tris(dimethylamino)phosphonium-hexafluorophosphate |
| b.p. | boiling point |
| DCM | dichloromethane |
| DEAD | diethyl azodicarboxylate |
| DMF | N,N-dimethylformamide |
| DMF-DMA | dimethylformamide-dimethylacetal (FLUKA) |
| Eq. | equivalent(s) |
| ESI | electrospray ionization |
| ES-MS | electron spray-mass spectroscopy |
| Et | ethyl |
| h | hour(s) |
| HOAc | acetic acid |
| m-CPBA | 3-chloroperoxybenzoic acid |
| MeOH | methanol |
| mm | minute(s) |
| m.p. | melting point |
| Py-BOP | benzotriazol-1-yl-oxy-tris-pyrrolidino-phosphonium hexafluorophosphate |
| rt | room temperature |
| satd. | saturated |
| THF | tetrahydrofuran |
| TLC | thin-layer chromatography |
| TOF-MS | time-of-flight mass spectroscopy |
| $t_R$ | retention times |

Example 1

{4-[3-(4-Chloro-phenyl)1H-pyrazol-4yl]-pyrimidin-2-yl}-[4-(4-methyl-piperazin-1-yl)-phenyl]-amine The solution of 150 mg (0.515 mMol) of 2-chloro-4-[3-(4-chloro-phenyl)-1H-pyrazol-4-yl]-pyrimidine in 5 mL of 1,4-dioxanes (Merck p.a. 9671) at rt is treated with 99 mg of 4-(4-methyl-piperazin-1-yl)-phenylamine (0,515 mMol, 1 Eq.) and 235 mg (2.06 mMol; 202 µl; 4 Eq.) of HCl (32%) (Fluka puriss 84416). The yellow suspension is stirred for 24 h at 100° C. After cooling to rt, the supernatant is decanted and discarded. The smeary residue is treated with 10 ml of NaHCO$_3$ satd. solution and 10 ml of ethyl acetates. The precipitated crude product is filtered off and dried at 60° C. under reduced pressure. The combined organic layers are re-extracted with water, dried (Na$_2$SO$_4$), and evaporated to obtain additional crude product. The combined crude products are purified by means of column chromatography over silica gel (Si60 (0,040-0,063 mm) Merck); eluting with CH$_2$Cl$_2$/CH$_3$OH/NH$_4$OH (9:1:0.1). Final purification is done by suspending the obtained beige crystals in CH$_2$Cl$_2$/CH$_3$OH (1:1) to obtain {4-[3-(4-chloro-phenyl)-1H-pyrazol-4-yl]-pyrimidin-2-yl}-[4-(4-methyl-piperazin-1-yl)-phenyl]-amine as pure crystals.

Title compound: m.p.: 282-284° C.; ES-MS: 444.3 [M−H]$^−$; single peak at $t_R$=3.45 min (System 1); R$_f$=0.37 (CH$_2$Cl$_2$/MeOH/NH$_3$ 90:10:1).

General Synthetic Scheme 1:

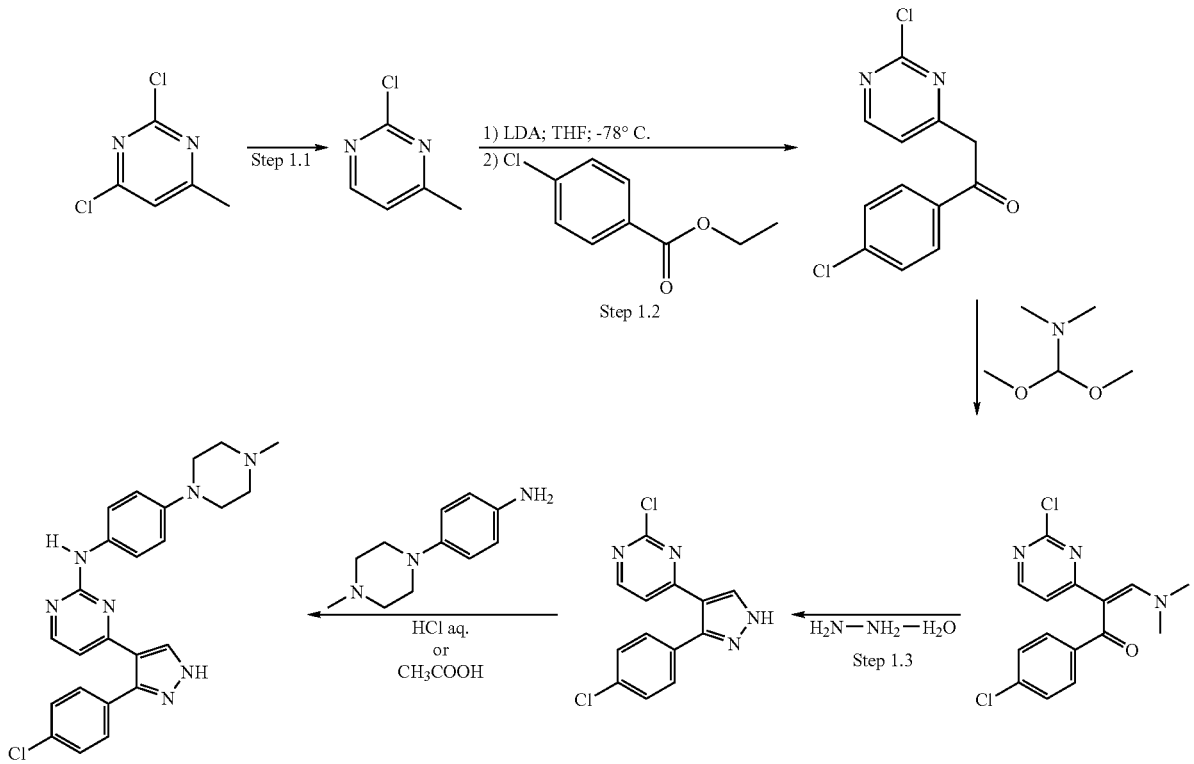

Example 1

4-(4-Methyl-piperazin-1-yl)-phenylamine is prepared as follows:

Step A: 50 g (0.247 Mol) of 1-Bromo-4-nitro-benzene and 55 mL. (0.495 Mol) of 1-methyl-piperazine are heated for 26 h at 80° C. After cooling, the reaction mixture is taken up in water and extracted with $CH_2Cl_2CH_3OH$ (8:2). The combined organic layers are dried ($Na_2SO_4$), filtered and evaporated under reduced pressure. The crude product is recrystallized from ethanol to obtain 1-methyl-4-(4-nitro-phenyl)-piperazine. Title compound: ES-MS: 443.0 $[M+H]^+$; $R_f$=0.38 ($CH_2Cl_2$/MeOH 9:1).

Step B: 44.3 g (0.2 Mol) of 1-Methyl-4-(4-nitro-phenyl)-piperazine is dissolved in 1200 mL of $CH_3OH$ and subjected to catalytic hydration at rt using Raney-Ni (10 g) as catalyst. After filtration over Celite, the crude product is purified via solid-distillation (0.16 mbar, 180° C.; heat temp 125° C.) to obtain 4-(4-methyl-piperazin-1-yl)-phenylamine. Title compound: ES-MS: 192.1 $[M+H]^+$; single peak at $t_R$=1.08 min (System 1); $R_f$=0.33 ($CH_2Cl_2$/MeOH 4:1).

Step 1.1: 2-Chloro-4-methyl-pyrimidine 200 g (227 Mol) of 2,4-Dichloro-6-methylpyrimidine is suspended in 2 l of water/ethanol (1:1) and heated to 50° C. under stirring. Upon dissolution, 331.3 g (5.07 Mol; 4.13 Eq.) of zinc dust (Fluka 96454) is added, followed by 10 crystals of iodine (Merck p.a. 4761.0100). After stirring for 20 h at 50° C., the grey suspension is filtered over HYFLO (Hyflo Super Cel®; Fluka), washed with few ethanol and diluted with 800 mL of water. The mixture is extracted with tert-butylmethyl ether, the organic layer washed with brine, dried ($Na_2SO_4$), filtered and evaporated under reduced pressure at 40° C. to obtain 2-chloro-4-methyl-pyrimidine as beige crystals.

Title compound: m.p.: 44-47° C.; single peak at $t_R$=2.92 min (System 1); $R_f$=0.5 (ethyl acetate).

Step 1.2: 1-(4-Chloro-phenyl)-2-(2-chloro-pyrimidin-4-yl)-ethanone

To the solution of 19 mL (38 mMol) of LDA (Lithiumdiisopropylamide) (~2 M in THF/heptan/ethylbenzene; FLUKA pract 62491) at −74° C., under a flow of Argon, is added dropwise a solution of 2-chloro-4-methyl-pyrimidine (4.11 g; 32 mMol) in 20 mL of THF abs. After stirring the beige solution at −74° C. for 3 h, 7.01 g (38 mMol) of ethyl-4-chlorobenzoate (LANCASTER 1407) is added within 30 min. The reaction is continued for 21 h, allowing temperature to reach rt. 100 mL of water is added slowly followed by extraction with ethyl acetate. The combined organic layers are washed with water, dried ($Na_2SO_4$) and filtered. After removal of the solvent under reduced pressure, crude product is obtained. The crude product is suspended in ethyl acetate/hexanes (1:2). After filtering off and drying at 60° C., the orange crystals are recrystallized from methanol to obtain pure, yellowish 1-(4-chloro-phenyl)-2-(2-chloro-pyrimidin-4-yl)-ethanone.

Title compound: m.p.: 145-146° C.; ES-MS: 267 $[M+H]^+$; single peak at $t_R$=6.33 min (System 1).

Step 1.3: 2-Chloro-4-[3-(4-chloro-phenyl)-1H-pyrazol-4-yl]-pyrimidine 3.67 g (13.74 mMol) of 1-(4-Chloro-phenyl)-2-(2-chloro-pyrimidin-4-yl)-ethanone is suspended in 91.6 mL (50 Eq.) of N,N-dimethylformamid-dimethylacetal (Fluka puriss. 40271) and stirred for 2 h at 100° C. The dark brownish solution is freed from solvent under high vacuum at 30° C. The crude product, (Z)-1-(4-chloro-phenyl)-2-(2-chloro-pyrimidin-4-yl)-3-dimethylamino-propenone, is used for the next step without purification. To the solution of 5.42 g (14.2 mMol) of (Z)-1-(4-chloro-phenyl)-2-(2-chloro-pyrimidin-4-yl)-3-dimethylamino-propenone in 30 mL of ethanol 0.785 g (0.763 mL; 15.69 mMol, 1.1 Eq.) of hyrazine monohydrate (Fluka 53850) is added at rt. After stirring 45 min at rt, the yellow crystals are filtered off, washed with ethanol and dried at 60° C. under vacuum. The crude product is purified by recrystallization from methanol to obtain 2-chloro-4-[3-(4-chloro-phenyl)-1H-pyrazol-4-yl]-pyrimidine as slightly yellowish crystals.

Title compound: m.p.: 246-247° C. (decomposition temperature); ES-MS: 289 $[M+H]^+$; single peak at $t_R$=5.81 min (System 1); $R_f$=0.2 ($CH_2Cl_2$/MeOH 95:5).

Example 2

{4-[3-(4-Chloro-phenyl)-1H-pyrazol-4-yl]-pyrimidin-2-yl}-[4-(2-di methyl-amino-ethoxy)-phenyl]-amine The title compound is prepared as described in Example 1 using 4-(2-dimethylamino-ethoxy)-phenylamine.

4-(2-Dimethylamino-ethoxy)-phenylamine is prepared in 3 steps from p-nitrophenol:

Step A: To the solution of 27.83 g (0.2 Mol) of 4-nitrophenol (Fluka 73560) in 420 mL of acetone is added 55.28 g (0.4 Mol) of potassium carbonate, 143.42 g (1 Mol) of 1-bromo-2-chloro-ethane, 0.55 g (0.0033 Mol) of potassium iodide and 0.28 g (0.00087 Mol) of tetrabutyl-ammonium bromide (Fluka 86860). The resulting suspension is refluxed for 67 h. After removing the solvent under reduced pressure, the residue is taken up into ethyl acetate and washed with water. The combined organic layers are dried ($Na_2SO_4$), filtered and concentrated under reduced pressure. After trituration of the residue with ligroin, the crystals are filtered off to obtain 1-(2-chloro-ethoxy)-4-nitro-benzene.

Step B: 36 g (0.178 Mol) of 1-(2-Chloro-ethoxy)-4-nitrobenzene is dissolved in 360 mL of ethanol and subjected to catalytic hydration at rt using $PtO_2$ (1.5 g) as catalyst. The resulting suspension is diluted with $CH_2Cl_2$, filtered, and concentrated to approx. 150 mL. After cooling to 0° C. the crystals are filtered off, washed and dried at 60° C. under vacuum to obtain 4-(2-chloro-ethoxy)-phenylamine. Title compound: m.p.: 87-91° C.; ES-MS: 172 $[M+H]^+$; single peak at $t_R$=2.73 min (System 1).

Step C: 11.15 g (0.065 Mol) of 4-(2-Chloro-ethoxy)-phenylamine is suspended in 150 mL (1.18 Mol) of dimethylamine (40% in water; Fluka 38940) and heated under stirring in a steel pressure reactor at 4 bar for 21 h. After cooling the reaction mixture is diluted with 150 mL of 2N NaOH and extracted with ethyl acetate. The combined organic layers are washed with water, dried ($Na_2SO_4$), filtered and evaporated under reduced pressure to obtain 4-(2-dimethylamino-ethoxy)-phenylamine. Title compound: ES-MS: 181 $[M+H]^+$; single peak at $t_R$=1.10 min (System 1).

Example 3

{4-[3-(4-Chloro-phenyl)-1H-pyrazol-4-yl]-pyrimidin-2-yl}-[4-(2-diethylamino-ethoxy)phenyl]-amine The title compound is prepared as described in Example 1 using 4-(2-diethylamino-ethoxy)-phenylamine.

4-(2Diethylamino-ethoxy)-phenylamine is prepared as follows:

Step A: To the solution of 8.0 g (51 mMol) of 1-chloro-4-nitrobenzene and 6.0 g (6.8 mL; 51 mMol) of 2-diethylamino-ethanol in 50 mL of DMF at 0° C. is added 2.7 g of NaH portionwise over 2 h. After stirring another hour at rt, the reaction mixture is poured onto 300 mL of water and stirred. After filtering off some crystalline product, the aqeous layers are extracted with ethyl acetate. The combined organic layers are dried and evaporated to obtain diethyl-[2-(4-nitro-phenoxy)-ethyl]-amine. Title compound: ES-MS: 239 [M+H]$^+$; single peak at $t_R$=5.1 min (System 2).

Step B: 10 g (42 mMol) of Diethyl-[2-(4-nitro-phenoxy)-ethyl]-amine is dissolved in 100 mL of ethanol and subjected to catalytic hydration at rt using 894 mg of Pd/C. After filtration trough HYFLO and removal of the solvent under reduced pressure, the crude product is purified by bulb-to-bulb distillation (140° C.) to obtain 4-(2-diethylamino-ethoxy)-phenylamine. Title compound: ES-MS: 209 [M+H]$^+$; single peak at $t_R$=2.3 min (System 2).

Example 4

{4-[3-(4-Chloro-phenyl)-1H-pyrazol-4yl]-pyrimidin-2-yl}-[4-(2-morpholinyl-4-yl-ethoxy)-phenyl]-amine The title compound is prepared as described in Example 1 using 4-(2-morpholin-4-yl-ethoxy)-phenylamine.

4-(2-Morpholin-4-yl-ethoxy)-phenylamine is prepared as follows:

Step A: To the solution of 8.0 g (51 mMol) of 1-chloro-4-nitrobenzene and 6.7 g (6.3 mL; 51 mMol) of N-hydroxy-ethyl-morpholine in 50 mL of DMF at 0° C. is added 2.7 g of NaH portionwise over 2.5 h. After stirring another hour at rt, the reaction mixture is poured onto 200 mL of water and stirred. The precipitated crystals are filtered and dried at 60° C. under vacuum to obtain 4-[2-(4-nitro-phenoxy)-ethyl]-morpholine. Title compound: ES-MS: 253 [M+H]$^+$; single peak at $t_R$=4.8 min (System 2).

Step B: 8.1 g (32 mMol) of 4-[2-(4-Nitro-phenoxy)-ethyl]-morpholine is dissolved in 100 mL of ethanol and subjected to catalytic hydration at rt using 681 mg of Pd/C. After filtration trough HYFLO and removal of the solvent under reduced pressure, the crude product is purified by bulb-to-bulb distillation (0.13 mbar: 200° C.) to obtain 4-(2-morpholin-4-yl-ethoxy)-phenylamine. Title compound: ES-MS: 223 [M+H]$^+$; single peak at $t_R$=3 min (System 2).

Example 5

{4-[3-(3-Chloro-phenyl)-1H-pyrazol-4-yl]-pyrimidin-2-yl}-[4-(2-dimethylamino-ethoxy)-phenyl]-amine The title compound is prepared as described in Example 1 using 3-chloro-benzoic acid ethyl ester and 4-(2-dimethylamino-ethoxy)-phenylamine (see Example 2).

3-Chloro-benzoic acid ethyl ester is prepared from 3-chloro-benzoic acid using a standard protocol with ethanol/$H_2SO_4$ according to L.-F. Tietze & T. Eicher, Reactions and Syntheses in the Organic Chemistry Laboratory; University Science Books, Mill Valley, Calif., 1989). Title compound: single peak at $t_R$=7.29 min (System 1).

Example 6

{4-[3-(3Chloro-phenyl)1H-pyrazol-4-yl]-pyrimidin-2-yl}-[4-(2-morpholin-4yl-ethoxy)-phenyl]-amine The title compound is prepared as described in Example 1 using 3-chloro-benzoic acid ethyl ester (see Example 5) and 4-(2-morpholin-4-yl-ethoxy)phenylamine (see Example 4).

Example 7

{4-[3-(3-Chloro-phenyl)-1H-pyrazol-4-yl]-pyrimidin-2-yl}-[4-(2-diethylamino-ethoxy)-phenyl]-amine The title compound is prepared as described in Example 1 using 3-chloro-benzoic acid ethyl ester (see Example 5) and 4-(2-diethylamino-ethoxy)-phenylamine (see Example 3).

Example 8

{(4-[3-(3-Chloro-phenyl)-1H-pyrazol-4-yl]-pyrimidin-2-yl}-[4-(4-methyl-piperazin-1-yl)-phenyl]-amine The title compound is prepared as described in Example 1 using 3-chloro-benzoic acid ethyl ester (see Example 5).

Example 9

{4-[3-(4-Methoxy-phenyl)-1H-pyrazol-4-yl]-pyrimidin-2-yl}-[4-(4-methyl-piperazin-1-yl)-phenyl]-amine The title compound is prepared as described in Example 1 using 4-methoxy-benzoic acid ethyl ester (Aldrich W24,200-4).

Example 10

{4-[3-(4-Methoxy-phenyl)1H-pyrazol-4-yl]-pyrimidin-2-yl}-[4-(2-morpholin-4-yl-ethoxy)-phenyl]-amine The title compound is prepared as described in Example 1 using 4-methoxy-benzoic acid ethyl ester (Aldrich W24,200-4) and 4-(2-morpholin-4yl-ethoxy)-phenylamine (see Example 4).

Example 11

{4-[3-(4-Ethyl-phenyl)-1H-pyrazol-4-yl]-pyrimidin-2-yl}[4-(4-methyl-piperazin-1-yl)-phenyl]-amine The title compound is prepared as described in Example 1 using 4-ethyl-benzoic acid ethyl ester.

4Ethyl-benzoic acid ethyl ester is prepared from 4-ethyl-benzoic acid using a standard protocol with ethanol/$H_2SO_4$ according to L.-F. Tietze & T. Eicher, Reactions and Syntheses in the Organic Chemistry Laboratory; University Science Books, Mill Valley, Calif., 1989). Title compound: b.p. 132° C. (12 mm Hg); single peak at $t_R$=7.51 min (System 1).

Example 12

[4-(2-Diethylamino-ethoxy)phenyl]-{4-[3-(4-ethyl-phenyl)-1H-pyrazol-4-yl]-pyrimidin-2-yl}-amine The title compound is prepared as described in Example 1 using 4-ethyl-benzoic acid ethyl ester (see Example 11) and 4-(2-diethylamino-ethoxy)-phenylamine (see Example 3).

Example 13

[4-(2-Diethylamino-ethoxy)-phenyl]-{4-[3-(4-methoxy-phenyl)-1H-pyrazol-4yl]-pyrimidin-2-yl}-amine The title compound is prepared as described in Example 1 using 4-methoxy-benzoic acid ethyl ester (Aldrich W24,200-4) and 4-(2-diethylamino-ethoxy)-phenylamine (see Example 3).

Example 14

[4-(2-Diethylamino-ethoxy)phenyl]-{4-[43-(3-methoxy-phenyl)-1H-pyrazol-4-yl]-pyrimidin-2-yl}-amine The title compound is prepared as described in Example 1 using 3-methoxy-benzoic acid ethyl ester and 4-(2-diethylamino-ethoxy)-phenylamine (see Example 3).

3-Methoxy-benzoic acid ethyl ester is prepared from 3-methoxy-benzoic acid using a standard protocol with ethanol/H$_2$SO$_4$ according to L.-F. Tietze & T. Eicher, Reactions and Syntheses in the Organic Chemistry Laboratory; University Science Books, Mill Valley, Calif., 1989). Title compound: b.p. 151° C. (25 mm Hg); single peak at $t_R$=6.51 min (System 1).

Example 15

{4-[3-(3-Methoxy-phenyl)-1H-pyrazol-4yl]pyrimidin-2-yl}-[4-(2-morpholin-4-yl-ethoxy)-phenyl]-amine The title compound is prepared as described in Example 1 using 3-methoxy-benzoic acid ethyl ester (see Example 14) and 4-(2-morpholin-4-yl-ethoxy)-phenylamine (see Example 4).

Example 16

{4-[3-(3-Methoxy-phenyl)-1H-pyrazol-4-yl]-pyrimidin-2-yl}-[4-(4-methyl-piperazin-1-yl)-phenyl]-amine The title compound is prepared as described in Example 1 using 3-methoxy-benzoic acid ethyl ester (see Example 14).

Example 17

[4-(2-Dimethylamino-ethoxy)-phenyl]-{4-[3-(4-ethyl-phenyl)-1H-pyrazol-4-yl]-pyrimidin-2-yl}-amine The title compound is prepared as described in Example 1 using 4-ethyl-benzoic acid ethyl ester (see Example 11) and 4-(2-dimethylamino-ethoxy)-phenylamine (see Example 2).

Example 18

[4-(4-Methyl-piperazin-1yl)-phenyl]-[4-(3-m-tolyl-1H-pyrazol-4-yl)-pyrimidin-2-yl]-amine The title compound is prepared as described in Example 1 using ethyl-3-methylbenzoate (Aldrich 25,305-7).

Example 19

[4-(2-Diethylamino-ethoxy)-phenyl]-[4-(3-m-tolyl-1H-pyrazol-4-yl)-pyrimidin-2-yl]-amine The title compound is prepared as described in Example 1 using ethyl-3-methylbenzoate (Aldrich 25,305-7) and 4-(2-diethylamino-ethoxy)-phenylamine (see Example 3).

Example 20

[4-(2-Dimethylamino-ethoxy)-phenyl]-[4-(3-m-tolyl-1H-pyrazol-4-yl)-pyrimidin-2-yl]-amine The title compound is prepared as described in Example 1 using ethyl-3-methylbenzoate (Aldrich 25,3057) and 4-(2-dimethylamino-ethoxy)-phenylamine (see Example 2).

Example 21

{4-[3-(3,4-Dichloro-phenyl)-1H-pyrazol-4-yl]-pyrimidin-2-yl}-[4-(2-dimethylamino-ethoxy)-phenyl]-amine The title compound is prepared as described in Example 1 using ethyl-3,4-dichlorobenzoate and 4-(2-dimethylamino-ethoxy)-phenylamine (see Example 2).

Ethyl-3,4-dichlorobenzoate is prepared from 3,4-dichlorobenzoic acid using a standard protocol with ethanol/H$_2$SO$_4$ according to L.-F. Tietze & T. Eicher, Reactions and Syntheses in the Organic Chemistry Laboratory; University Science Books, Mill Valley, Calif., 1989). Title compound: m.p.: 40-41° C.; single peak at $t_R$=7.89 min (System 1).

Example 22

{4-[3-(3,4-Dichloro-phenyl)-1H-pyrazol-4-yl]-pyrimidin-2-yl}-[4-(4-methyl-piperazin-1-yl)-phenyl]-amine The title compound is prepared as described in Example 1 using ethyl-3,4-dichlorobenzoate (see Example 21).

Example 23

{4-[3-(4-Benzyloxy-phenyl)-1H-pyrazol-4-yl]-pyrimidin-2-yl}-[4-(2-dimethylamino-ethoxy)-phenyl]-amine The title compound is prepared as described in Example 1 using ethyl-4-(benzyloxy)benzoat (MAYBRIDGE 03-1741) and 4-(2-dimethylamino-ethoxy)-phenylamine (see Example 2).

Example 24

4-(4-{2-[4-(4-Methyl-piperazin-1-yl)-phenylamino]-pyrimidin-4-yl}1H-pyrazol-3-yl)-phenol The title compound is prepared as described in Example 1 using ethyl-4-(benzyloxy)benzoat (MAYBRIDGE 03-1741). The title compound is isolated as a side product due to the loss of the benzyl group.

Example 25

[4-(4-Methyl-piperazin-1-yl)-phenyl]-[4-(3-p-tolyl-1H-pyrazol-4-yl)-pyrimidin-2-yl]-amine The title compound is prepared as described in Example 1 using ethyl-p-toluate (Fluka 89909).

Example 26

[4-(2-Dimethylamino-ethoxy)-phenyl]-[4-(3-p-tolyl-1H-pyrazolyl-4-yl)-pyrimidin-2-yl]-amine The tile compound is prepared as described in Example 1 using ethyl-4-methylbenzoate (see Example 25) and 4-(2-dimethylamino-ethoxy)-phenylamine (see Example 2).

Example 27

{4-[3(4-Chloro-phenyl)-1H-pyrazol-4-yl]-pyrimidin-2-yl}-[3-(1-methyl-piperidin-4-ylmethoxy)-phenyl]-amine The title compound is prepared as described in Example 1 using [3-(1-methyl-piperidin-4-ylmethoxy)-phenyl]-carbamic acid tert-butyl ester.

[3-(1-Methyl-piperidin-4-ylmethoxy)-phenyl]-carbamic acid tert-butyl ester is prepared as Follows:

To the solution of 3.04 g (14.51 mMol; 1.25 Eq.) of 3-N-BOC-Aminophenol and 3.81 9 (14.51 mMol; 1.25 Eq.) of triphenylphosphin (Aldrich T8,440-9) under Argon in 30 mL of THF at 10° C. is added dropwise a solution of 2.26 mL (14.51 mMol) of diethyl-azodicarboxylate (95%; Fluka 11624) in 6 mL of THF abs. After stirring for 10 min under ice cooling, a solution of 1.5 g (11.61 mMol; 1 Eq.) of 1-methyl-4piperidinemethanol (Chem Pacific; 33077*) in 6 mL of THF abs. is added and kept for 20 min at 10° C. After 15 h at rt, the solvent is removed under reduced pres sure and the reaction mixture is purified by column chromatography over silica gel [Si60 (0,040-0,063 mm) Merck], eluting with methylenchlorid/methanol/$NH_3$ (25%$_{aqua}$) 70:10:0.8 to obtain [3-(1-methyl-piperidin-4-ylmethoxy)-phenyl]-carbamic acid tert-butyl ester. Title compound: ES-MS: 321.1 $[M+H]^+$; single peak at $t_R$=4.63 min (System 1).

* 1-Methyl-4-piperidinemethanol can alternatively be prepared from piperidin-4-yl-methanol and formaldehyde (36% in water) under reductive conditions ($H_2$/RaNi in $CH_3OH$) at rt.

Example 28

{4-[3-(4-Chloro-phenyl)-1H-pyrazol-4-yl]-pyrimidin-2-yl}-[4-(1-methyl-piperidin-4-ylmethoxy)-phenyl]-1-amine The title compound is prepared as described in Example 1 using [4-(1-methyl-piperidin-4-ylmethoxy)-phenyl]-carbamic acid tert-butyl ester.

[4-(1-Methyl-piperidin-4-ylmethoxy)-phenyl]-carbamic acid tert-butyl ester is prepared as described for [3-(1-methyl-piperidin-4-ylmethoxy)-phenyl]-carbamic acid tert-butyl ester (see Example 27) using 4-N-BOC-Aminophenol (AstaTech; B56686). Title compound: ES-MS: 321.1 $[M+H]^+$; single peak at $t_R$=4.55 min (System 1).

Example 29

{4-[3-(4-Chloro-phenyl)-1H-pyrazol-4-yl]-pyrimidin-2-yl}-[3-(4-methyl-piperazin-1-yl)-phenyl]-amine The title compound is prepared as described in Example 1 using 3-(4-methyl-piperazin-1-yl)-phenylamine.

3-(4-Methyl-piperazin-1-yl)-phenylamine is prepared as described for 4-(4-methyl-piperazin-1-yl)-phenylamine (see Example 1) using 3-bromo-phenylamine.

Title compound: ES-MS: 192.0 $[M+H]^+$; single peak at $t_R$=1.14 min (System 1).

Example 30

4-{4-[3-(4-Chloro-phenyl)-1H-pyrazol-4-yl]-pyrimidin-2-ylamino}-benzoic acid

The title compound is prepared as described in Example 1 using 4-aminobenzoic acid (Fluka 06930).

Example 31

(4-{4-[3-(4-Chloro-phenyl)-1H-pyrazol-4-yl]-pyrimidin-2-ylamino}-phenyl)-(4-methyl-piperazin-1-yl)-methanone To the suspension of 600 mg (1.53 mMol; 1 Eq.) of 4-{4-[3-(4-chloro-phenyl)1H-pyrazol-4-yl]-pyrimidin-2-ylamino}-benzoic acid (Example 30) in 5 mL of DMF at rt is added 186 mg (202 μL; 1.83 mMol; 1.2 Eq.) of N-methylmorpholine (Fluka 67869); 677 mg (1.53 mMol; 1 Eq.) of BOP (Fluka 12802) and 153 mg (170 μL; 1.53 mMol; I Eq.) of N-methylpiperazine (Fluka 68810). After 2 h at rt, the yellow solution is treated with 50 mL of $NaHCO_3$ satd. solution and extracted with ethyl acetate. The combined organic layers are washed with water, dried ($Na_2SO_4$), filtered and concentrated under reduced pressure to approx. 10 mL. The precipitated crystals are collected, washed with a little ethyl acetate and dried at 60° C. under vacuum to obtain (4-{4-[3-(4-chloro-phenyl)-1H-pyrazol-4-yl]-pyrimidin-2-ylamino}-phenyl)-(4methyl-piperazin-1-yl)-methanone.

Example 32

{4-[3-(4-Chloro-phenyl)-1H-pyrazol-4-yl]-pyrimidin-2-yl}-[4-(4-methyl-piperazin-1-ylmethyl)-phenyl]-amine To the suspension of 96 mg (2.53 mMol; 4 Eq.) of lithium aluminum hydride (Fluka 62420) in 20 mL of THF abs. under Argon at rt is added slowly within 10 min 300 mg (0.633 mMol) of (4-{4-([3-(4-chloro-phenyl)-1H-pyrazol-4-yl]-pyrimidin-2-ylamino}-phenyl)-(4-methyl-piperazin-1-yl)-methanone (see Example 31) as a solid; under vigorous foaming. After stirring for 2.5 h at rt, the suspension is cooled to 0° C. and treated dropwise with 20 mL of water. After diluting further with 50 mL of water, the suspension is extracted with ethyl acetate. The combined organic layers are washed with water, dried ($Na_2SO_4$), filtered and concentrated under reduced pressure. The crude product is purified over silica gel, eluting with $CH_2Cl_2/CH_3OH$ (4:1) followed by trituration in diethyl ether to obtain {4-[3-(4-chloro-phenyl)-1H-pyrazol-4-yl]-pyrimidin-2-yl}-[4-(4-methyl-piperazin-1-ylmethyl)-phenyl]-amine.

General Synthetic Scheme 2:

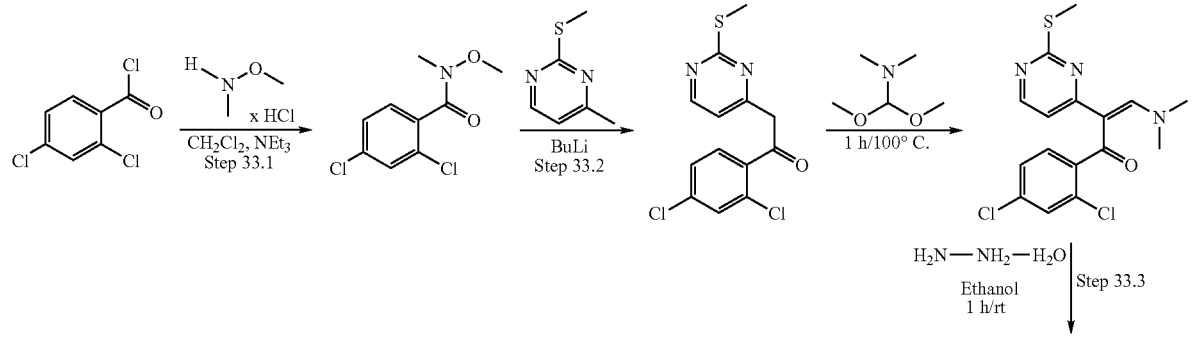

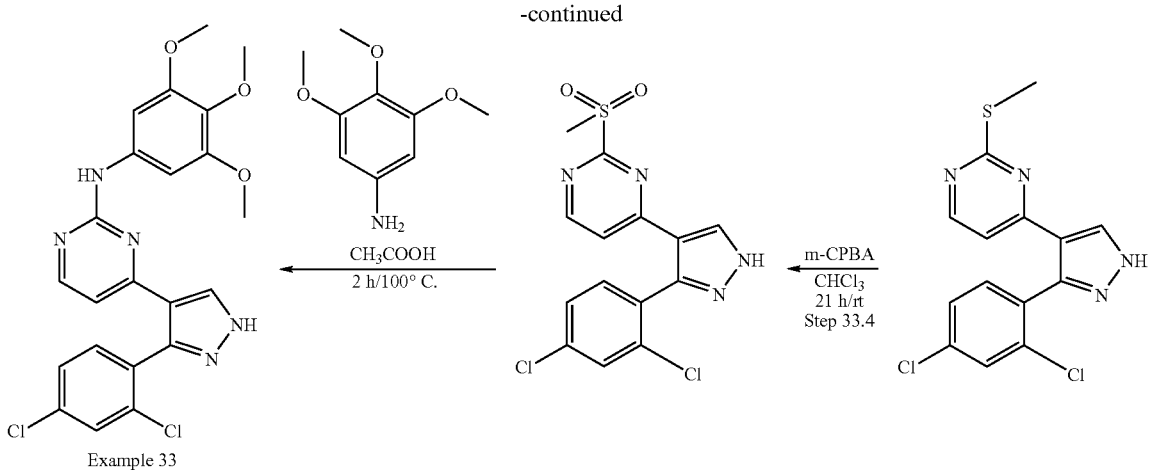

Example 33

Example 33

{4-[3-(2,4-Dichloro-phenyl)-1H-pyrazol-4-yl]-pyrimidin-2-yl}-(3,4,5-trimethoxy-phenyl)-amine {4-[3-(2,4-Dichloro-phenyl)-1H-pyrazol-4-yl]-pyrimidin-2-yl}-(3,4,5-trimethoxy-phenyl)-amine is synthesized from 4-[3-(2,4-dichloro-phenyl)-1H-pyrazol-4-yl]-2-methanesulfonyl-pyrimidine in analogy to a literature procedure (Klutchko et al., Journal of Medicinal Chemistry, 1998, Vol. 41, No. 17, 3276-3292) using 3,4,5-trimethoxyaniline (Fluka 92129) and glacial HOAc.

Step 33.1: 2,4-Dichloro-N-methoxy-N-methyl-benzamide

The title compound is prepared in analogy to a standard protocol using 2,4-dichloro-benzoyl chloride (Aldrich 11, 193-7) and N—O-dimethylhydroxylamine HCl (Fluka 40706) in $CH_2Cl_2$ (Nahm, Steven; Weinreb, Steven M.; *Tetrahedron Lett.*; 1981; 22 (39); 3815-3818).

Step 33.2: 1-(2,4-Dichloro-phenyl)-2-(2-methylsulfanyl-pyrimidin-4-yl)-ethanone

To the solution of 85 mL of diisopropylamine (Fluka 38300) and 2.5 L of THF at −75° C. under Argon is added 370 mL (0.55 Mol) of butyl lithium (BuLi; 1.6N in hexanes; Fluka 20160) within 1 h. To this is added 71 g (0.5 Mol) of 4-methyl-2-methylsulfanyl-pyrimidine in 250 mL of $CH_2Cl_2$ at −75° C. within 30 min. After this, a solution of 118 g (0.5 Mol) of 2,4dichloro-N-methoxy-N-methyl-benzamide in 250 mL of $CH_2Cl_2$ at −75° C. within 30 min followed by letting the mixture warm up to rt. After completion, the reaction mixture is poured onto 7 L of $NH_4Cl$ satd. and extracted with ethyl acetate. The combined organic layers are washed with brine, dried and evaporated. The crude product is suspended in hexanes. After filtering off and drying 1-(2,4-dichloro-phenyl)-2-(2-methylsulfanyl-pyrimidin-4-yl)-ethanone is obtained as yellow crystals. Title compound: m.p.: 105-107° C.; ES-MS: 313.0/314.9 $[M+H]^+$.

4-Methyl-2-methylsulfanyl-pyrimidine is prepared from 4-methyl-pyrimidine-2-thiol in analogy to a standard protocol using methyliodide (Strekowskl, L.; Wydra, R. L.; Janda, L.; Harden, D. B. *J. Org. Chem.* (1991), 56(19), 5610-14). Title compound: single peak at 3.94 min (System 1); $R_f$=0.32 (ethyl acetate/hexane 1:2).

Step 33.3: 4-[3-(2,4-Dichloro-phenyl)-1H-pyrazol-4-yl]-2-methylsulfanyl-pyrimidine The title compound is prepared from 1-(2,4-dichloro-phenyl)-2-(2-methylsulfanyl-pyrimidin-4-yl)-ethanone as described in Example 1, Step 1.3, using N,N-dimethylformamid-dimethylacetal and hydrazine monohydrate. Title compound: m.p.: 218-219° C.; single peak at 6.07 min (System 1).

Step 33.4: 4-[3-(2,4-Dichloro-phenyl)-1H-pyrazol-4-yl]-2-methanesulfonyl-pyrimidine The title compound is prepared from 4-[3-(2,4-dichloro-phenyl)-1H-pyrazol-4-yl]-2-methylsulfanyl-pyrimidine in analogy to a literature procedure (Klutchko et al., Journal of Medicinal Chemistry, 1998, Vol. 41, No. 17, 3276-3292) using m-CPBA (Fluka 25800) in $CHCl_3$. Title compound: ES-MS: 368.9 $[M+H]^+$; single peak at $t_R$=4.98 min (System 1); $R_f$=0.38 (ethyl acetate).

Example 34

{4-[3-(2,4-Dichloro-phenyl)-1H-pyrazol-4yl]-pyrimidin-2-yl}-[4-(4-methyl-piperazin-1-yl)-phenyl]-amine The title compound is prepared as described in Example 33 using 4-(4-methyl-piperazin-1-yl)-phenylamine (see Example 1).

Example 35

N(4-{4-[3-(4-Chloro-phenyl)-1H-pyrazol-4-yl]-pyrimidin-2-yl}-N',N'-dimethyl-benzene-1,3-diamine The title compound is prepared as described in Example 1 using 3-amino-N,N-dimethylaniline dihydrochloride (Fluka 07765).

Example 36

{4-[3-(4-Ethoxy-phenyl)-1H-pyrazol-4-yl]-pyrimidin-2-yl}-[4-(4-methyl-piperazin-1-yl)-phenyl]-amine The title compound is prepared as described in Example 33 using ethyl-4-ethoxybenzoate 97% (ACROS 346590250) and 4-(4-methyl-piperazin-1-yl)phenylamine (see Example 1).

Example 37

{4-[3-(4-Ethoxy-phenyl)-1H-pyrazol-4-yl]-pyrimidin-2-yl}-(3,4,5-trimethoxy-phenyl)-amine The title compound is prepared as described in Example 33 using 4-ethoxy-benzoic acid ethyl ester (ACROS 346590250) and 3,4,5-trimethoxyaniline (Fluka 92129).

Physicochemical Data:

| Example | melting point from | melting point to | HPLC [min]/ System | mass spectra; ESI; m/z = |
|---|---|---|---|---|
| 1 | 282 | 284 | 3.45/1 | 444.3 [M − H]⁻ |
| 2 | 236 | 239 | 3.48/1 | 435 [M + H]⁺ |
| 3 | 191 | 192 | 3.74/1 | 463 [M + H]⁺ |
| 4 | 244 | 247 | 3.53/1 | 477 [M + H]⁺ |
| 5 | 182 | 183 | 3.46/1 | 435 [M + H]⁺ |
| 6 | 192 | 193 | 3.54/1 | 477 [M + H]⁺ |
| 7 | 179 | 181 | 3.74/1 | 463 [M + H]⁺ |
| 8 | 297 | 299 | 3.43/1 | 446 [M + H]⁺ |
| 9 | 273 | 277 | 3.15/1 | 442.0 [M + H]⁺ |
| 10 | 232 | 234 | 3.23/1 | 473.0 [M + H]⁺ |
| 11 | 282 | 283 | 3.75/1 | 457.2 [M + H]⁺ |
| 12 | 206 | 207 | 4.01/1 | 440.2 [M + H]⁺ |
| 13 |  |  | 3.44/1 | 459.0 [M + H]⁺ |
| 14 |  |  | 3.48/1 | 459.3 [M + H]⁺ |
| 15 |  |  | 3.28/1 | 473.2 [M + H]⁺ |
| 16 |  |  | 3.17/1 | 442.2 [M + H]⁺ |
| 17 | 242 | 244 | 3.77/1 | 429.1 [M + H]⁺ |
| 18 | 280 | 282 | 3.38/1 | 426.1 [M + H]⁺ |
| 19 | 181 | 182 | 3.68/1 | 440.2 [M + H]⁺ |
| 20 | 206 | 207 | 3.41/1 | 415.1 [M + H]⁺ |
| 21 | 188 | 191 | 3.73/1 | 469.0 [M + H]⁺ |
| 22 | 300 | 307 | 3.70/1 | 479.9 [M + H]⁺ |
| 23 | 213 | 216 | 3.63/1 | 507.0 [M + H]⁺ |
| 24 | 305 | 309 | 2.40/1 | 428.1 [M + H]⁺ |
| 25 | 289 | 294 | 3.43/1 | 426.0 [M + H]⁺ |
| 26 | 251 | 259 | 3.45/1 | 415.1 [M + H]⁺ |
| 27 | 225 | 228 | 4.15/1 | 475.0 [M + H]⁺ |
| 28 | 270 | 274 | 3.73/1 | 475.0 [M + H]⁺ |
| 29 | 274 | 277 | 3.82/1 | 446.0 [M + H]⁺ |
| 30 | 342 | 349 | 4.53/1 | 391.9 [M + H]⁺ |
| 31 | 173 | 175 | 3.63/1 | 473.9 [M + H]⁺ |
| 32 | 240 | 242 | 3.41/1 | 460.0 [M + H]⁺ |
| 33 | 125 | 127 | 4.96/1 | 472.0 [M + H]⁺ |
| 34 | 263 | 265 | 3.52/1 | 477.9 [M + H]⁺ |
| 35 |  |  | 3.90/1 | 391.2 [M + H]⁺ |
| 36 |  |  | 3.37/1 | 456.2 [M + H]⁺ |
| 37 | 293 | 297 | 4.71/1 |  |

General Synthetic Scheme 3:

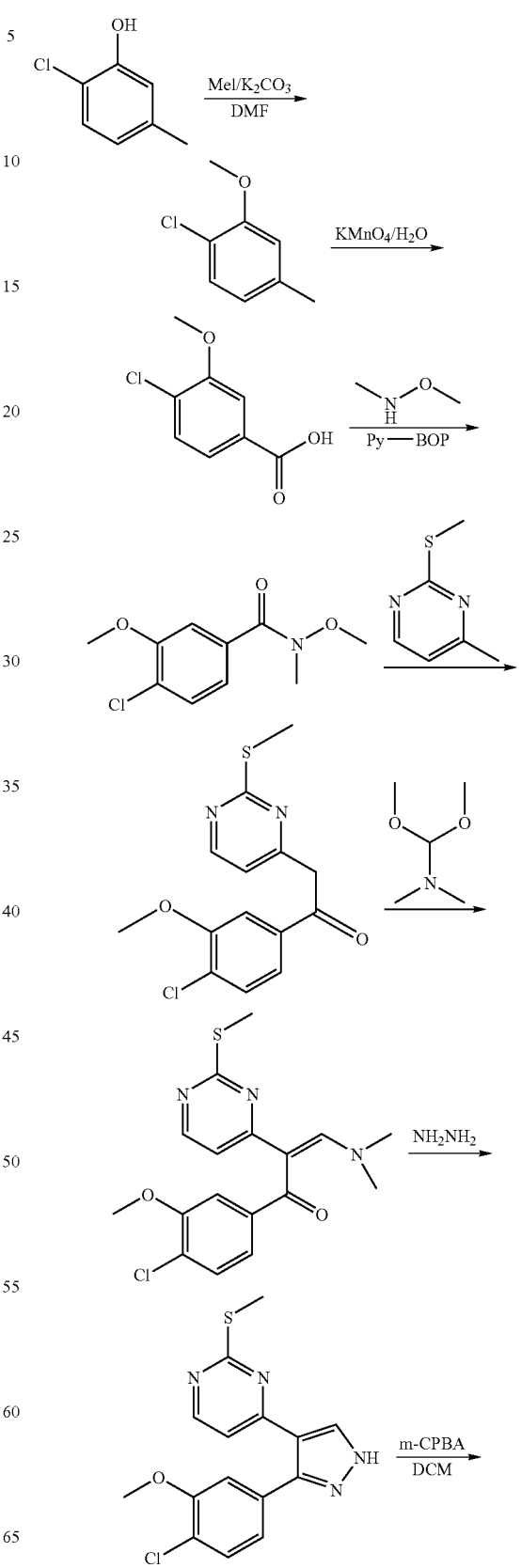

-continued

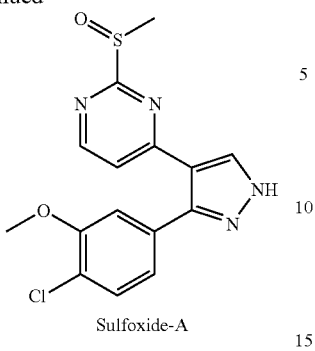
Sulfoxide-A

General synthetic scheme 4:

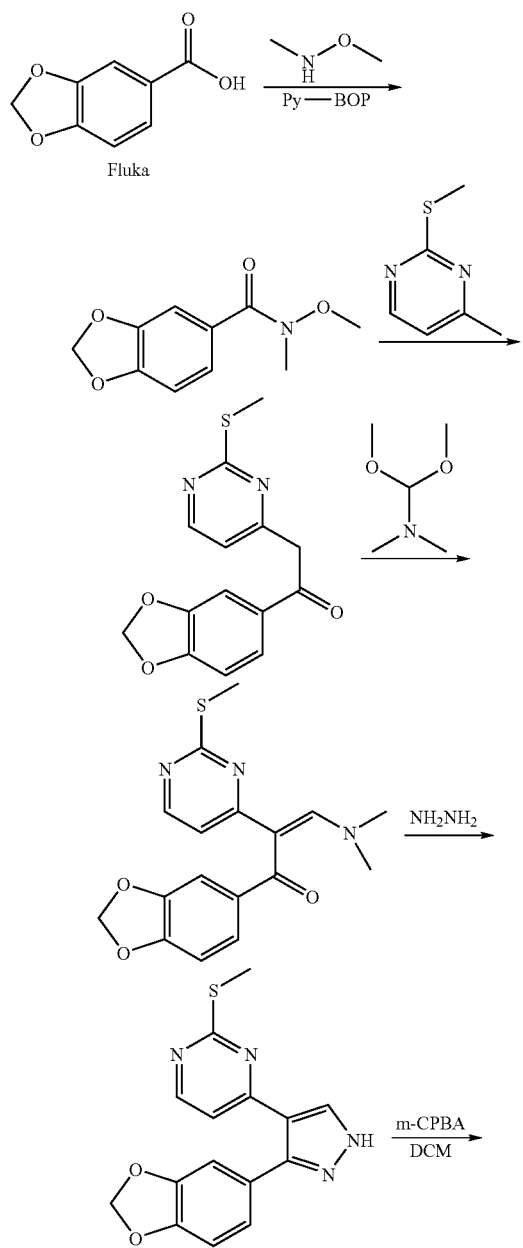

-continued

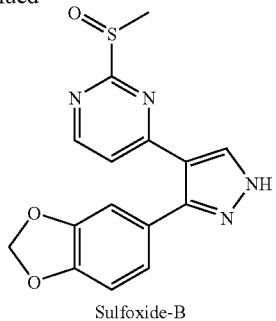
Sulfoxide-B

Sulfoxide-A and Sulfoxide-B can be prepared in analogy to the preparation of the sulfone of Example 33 beginning with 4-chloro-3-methoxy-benzoic acid and benzo[1,3]dioxole-5-carboxylic acid (Fluka), respectively, whereby the preparation of 4-chloro3-methoxy-benzoic acid is known in the art (see also 'General synthetic scheme 3').

Example 38

{4-[3-(4-Chloro-3-methoxy-phenyl)-1H-pyrazol-4-yl]-pyrimidin-2-yl}-(3,4,5-trimethoxy-phenyl)-amine Sulfoxide-A (100 mg, 0.28 mmoles) and the 3,4,5-trimethoxy aniline (524.9 mg, 2.86 mmoles) are dissolved in 1,4-dioxane (2 mL). The reaction mixture is stirred at rt for 10 min, then $BF_3.Et_2O$ (0.36 mL, 2.86 mmoles) is added to above mixture dropwise at rt. The yellow solution is stirred for 30 min at rt then heated to 100° C. overnight. After cooling to rt, the reaction is quenched with water. The aqueous phase is extracted with ethyl acetate. The combined organic phases are dried over sodium sulfate, concetrated and chromatographed on $SiO_2$ (50-80% EtOAc/Hexanes) to afford the title compound as a light yellow solid: ES-MS 468.1428 [M+H]; single peak at $t_R$=5.28 min (System 3); $R_f$=0.58 (100% EtOAc).

Example 39

3-{4-[3(4-Chloro-3-hydroxy-phenyl)-1H-pyrazol-4-yl]-pyrimidin-2-ylamino}-benzenesulfonamide 3-{4-[3-(4-Chloro-3-methoxy-phenyl)-1H-pyrazol-4-yl]-pyrimidin-2-ylamino}-benzenesulfonamide (Example 40) (94 mg, 0.2057 mmoles) is suspended in $CH_2Cl_2$ (20 mL) and cooled to −0° C. $BBr_3$ (0.5 mL, 1M in $CH_2Cl_2$) is added dropwise at −0° C. After 10 min the suspension is warmed to rt and kept at that temperature overnight. The reaction is quenched with 1 mL of water and the reaction mixture is concentrated. The residue is chromatographed on $SiO_2$ (3% methanol/$CH_2Cl_2$) affording the title compound: ES-MS 443.1 [M+H]; single peak at $t_R$=4.318 min (System 3); $R_f$=0.53 (100% EtOAc).

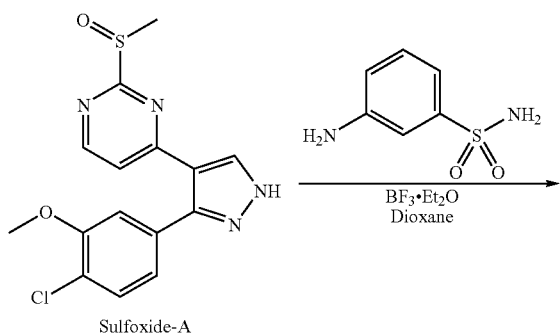

Sulfoxide-A

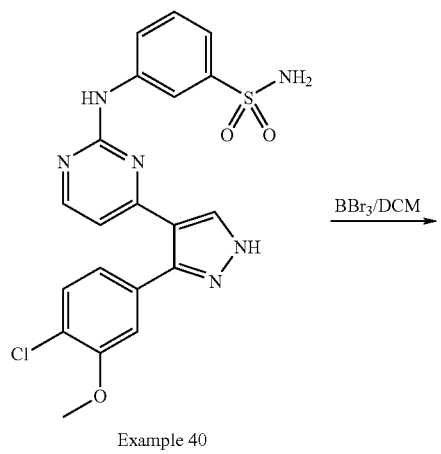

Example 40

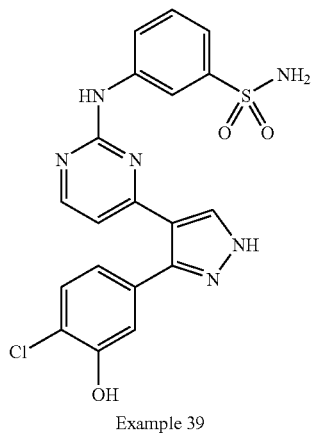

Example 39

Example 40

3-{4-[3-(4-Chloro-3-methoxy-phenyl)-1H-pyrazol-4-yl]-pyrimidin-2-ylamino}-benzenesulfonamide Sulfoxide-A (200 mg, 0.572 mmoles) and 3-aminobenzenesulfonamide (680 mg, 3.94 mmoles) are dissolved in 1,4-dioxane (6 mL). The reaction mixture is stirred at rt for 5 min, then $BF_3.Et_2O$ (0.72 mL, 5.76 mmoles) is added dropwise at rt. The reaction mixture is stirred 10 min at rt, then heated to 100° C. overnight. After cooling to rt the reaction is quenched with water and the aqueous phase is extracted with ethyl acetate. The combined organic phases are dried over sodium sulfate, concentrated and chromatographed on $SiO_2$ (linear gradient 50→80% EtOAc in Hexanes) affording the title compound as a light yellow solid: ES-MS 457.0869 [M+H]; single peak at $t_R$=4.930 min (System 3); $R_f$=0.58 (100% EtOAc).

Example 41

3-{4-[3-(4-Chloro-3-methoxy-phenyl)-1H-pyrazol-4-yl]-pyrimidin-2-ylamino}-benzoic acid ethyl ester Sulfoxide-A (50 mg, 0.143 mmoles) and 3-amino-benzoic acid ethyl ester (300 mg, 10.1 mmoles) are dissolved in 1,4-dioxane (2 mL). The reaction mixture is stirred at rt for 5 min, then $BF_3.Et_2O$ (0.36 mL, 2.86 mmoles) is added to the reaction mixture dropwise at rt. The reaction mixture is stirred 10 min at rt then heated to 100° C. overnight. After cooling to rt, the reaction mixture is diluted with water and a white solid precipitated from solution. The solid is washed with methanol to give the title compound: ES-MS 450.1350 [M+H]; single peak at $t_R$=6.10 min (System 3).

Example 42

3-{4-[3-(4-Chloro-3-hydroxy-phenyl)-1H-pyrazol-4-yl]-pyrimidin-2-ylamino}-benzoic acid ethyl ester 3-{4-[3-(4-Chloro-3-methoxy-phenyl)-1H-pyrazol-4-yl]-pyrimidin-2-ylamino}-benzoic acid ethyl ester (Example 41) (18 mg, 0.04 mmoles) is suspended in $CH_2Cl_2$ (2 mL) and cooled to −5° C. $BBr_3$ (0.5 mL, 1M in $CH_2Cl_2$) is added dropwise at −5° C. After 10 min the suspension turns to a clear brown solution. After 2 h at −5° C. another 0.5 mL of $BBr_3$ is added to the reaction mixture. Then the reaction mixture is warmed to rt and kept at that temperature for 30 min. The reaction is quenched with 5 mL water and stirred at rt overnight. The reaction mixture is extracted with ethyl acetate. The combined organic phases are dried over sodium sulfate, concentrated and chromatographed on $SiO_2$ (80% EtOAc/Hexanes) affording the title compound: ES-MS 436.1178 [M+H]; single peak at $t_R$=5.579 min (System 3).

Example 43

1-(3-{4-[3-(4-Chloro-3-methoxy-phenyl)-1H-pyrazol-4-yl]-pyrimidin-2-ylamino}-phenyl)-ethanone Sulfoxide-A (50 mg, 0.14 mmoles) and 1-(3-amino-phenyl)-ethanone (300 mg, 2.22 mmoles) are dissolved in 1,4-dioxane (2 mL). The reaction mixture is stirred at rt for 5 min, then $BF_3.Et_2O$ (0.36ml, 2.86 mmoles) is added to above mixture dropwise at rt. The reaction mixture is stirred 10 min at rt, then heated to 100° C. overnight. After cooling to rt, the reaction mixture is diluted with CH₂Cl₂, then washed with water. The organic layer is separated and concentrated. The residue is washed with CH₂Cl₂ and MeOH to afford the title compound as a solid: ES-MS 420.1232 [M+H]; single peak at $t_R$=5.29 min (System 3); $R_f$=0.60 (100% EtOAc).

Example 44

Benzothiazol-6-yl-{4-[3-(4-chloro-3-methoxy-phenyl)-1H-pyrazol-4-yl]-pyrimidin-2-yl}-amine Sulfoxide-A (100 mg, 0.286 mmoles) and benzothiazol-6-ylamine (430 mg, 2.86 mmoles) are dissolved in 1,4-dioxane (2 mL). The reaction mixture is stirred at rt for 10 min, then BF₃·Et₂O (0.36 mL, 2.86 mmoles) is added dropwise at rt. The yellow solution is stirred 10 min at rt then heated to 100° C. overnight. After cooling to rt, the reaction mixture is quenched with water. The aqueous phase is extracted with ethyl acetate. The combined organic phases are dried over sodium sulfate, concentrated and chromatographed on SiO₂ (linear gradient 50→80% EtOAc in Hexanes) to obtain the title compound as a light yellow product ES-MS 435.0773 [M+H]; single peak at $t_R$=5.14 min (System 3); $R_f$=0.50 (100% EtOAc).

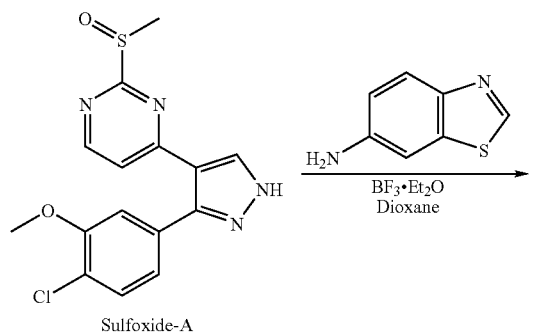

Sulfoxide-A

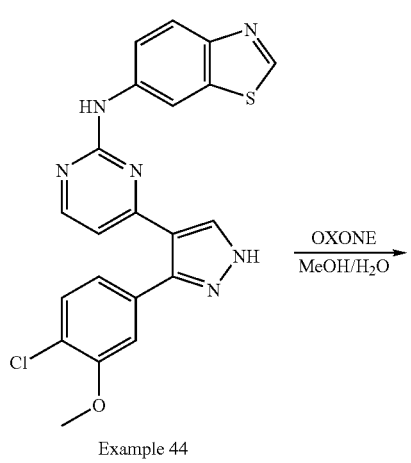

Example 44

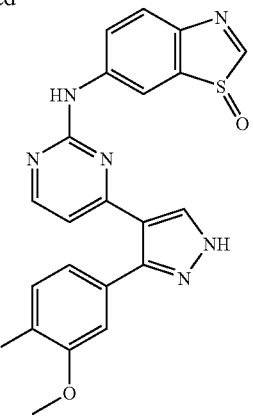

Example 45

Example 45

{4-[3-(4-Chloro-3-methoxy-phenyl)-1H-pyrazol-4-yl]-pyrimidin-2-yl}-(1-oxo-benzothiazol-6-yl)-amine A solution of OXONE (=KHSO₅; 141.4 mg, 0.23 mmoles) in water (2 mL) is added dropwise to a suspension of benzothiazol-6-yl-{4-[3-(4-chloro-3-methoxy-phenyl)-1H-pyrazol-4-yl]-pyrimidin-2-yl}-amine (Example 44) (20 mg, 0.046 mmoles) in methanol (2 mL) at rt. After stirring overnight at rt the suspension is diluted with water upon which the suspension turns to a clear yellow solution. The reaction mixture is extracted with ethyl acetate. The combined organic phases are dried over sodium sulfate, concentrated and chromatographed on SiO₂ (5% MeOH/CH₂Cl₂) to yield the title compound as light yellow solid: ES-MS 451.0751 [M+H]; single peak at $t_R$=4.93 min (System 3).

Example 46

[4-(3-Benzo[1,3]dioxol-5-yl-1H-pyrazol-4-yl)-pyrimidin-2-yl]-(3,4,5-trimethoxy-phenyl)-amine Sulfoxide-B (50 mg, 0.1 522 mmoles) and 3,4,5-trimethoxy aniline (278.8 mg, 1.522 mmoles) are dissolved in 1,4-dioxane (2 mL). The reaction mixture is stirred at rt for 10 min, then BF₃·Et₂O (0.19 mL, 1.522 mmoles) is added dropwise at rt. The reaction mixture is stirred 10 min at rt, then heated to 100° C. overnight. After cooling to rt the reaction is quenched with water. The aqueous phase is extracted With ethyl acetate. The combined organic phases are dried over sodium sulfate, concetrated and chromatographed on SiO₂ (linear gradient 50→80% EtOAc in Hexanes) affording the title compound as a light yellow solid: ES-MS 448.1608 [M+H]; single peak at $t_R$=4.579 min (System 3); $R_f$=0.58 (100% EtOAc).

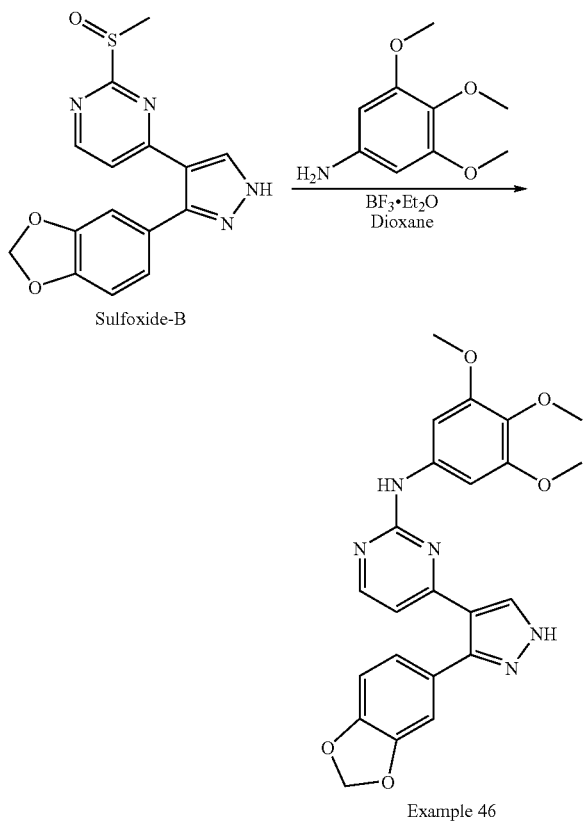

Example 47

3-[4-(3-Benzo[1,3]dioxol-5-yl-1H-pyrazol-4-yl)pyrimidin-2-ylamino]-benzoic acid tert-butyl ester Sulfoxide-B (206.6 mg, 0.63 mmol) and t-butyl-3-amino benzoate (370.5 mg, 1.92 mmol) are dissolved in THF (30 mL). The reaction mixture is stirred at rt and BF$_3$.etherate (0.2 mL, 1.58 mmol) is added. After 4 days at 80-100° C. more BF$_3$.etherate (0.1 mL, 0.79 mmol) is added. The reaction mixture is heated for 1 h at 100° C., cooled to rt, and poured over saturated NaCl (aq.). The crude product is extracted with EtOAc and the combined organic layers are dried over MgSO$_4$, filtered, concentrated, chromatographed on SiO$_2$ (0.5-5% MeOH/CH$_2$Cl$_2$), and recrystallized (THF/Hexane) to yield the title compound as an off-white solid: TOF-MS 458.1791 (M+H$^+$); single peak at $t_R$=17.077 min (System 5); $R_f$=0.5 (10% MeOH, 1% NH$_4$OH in CH$_2$Cl$_2$).

Example 48

3-[4-(3-Benzo[1,3]dioxol-5-yl-1H-pyrazol-4-yl)-pyrimidin-2-ylamino]-benzenesulfonamide To Sulfoxide-B (378 mg, 1.15 mmol) and 3-amino-benzenesulfonamide (992 mg, 5.76 mmol) in 1,4-dioxane is added BF$_3$.etherate (364 µL, 2.88 mmol). The reaction mixture is refluxed for 16 h at 100° C., cooled to rt, and concentrated under reduced pressure. The residue is mixed with a minimum amount of water and extracted with EtOAc. The combined extracts are dried over MgSO$_4$, filtered, and concentrated. The residue is chromatographed on SiO$_2$ (2-5% MeOH/CH$_2$Cl$_2$) to yield an orange solid. The orange solid is dissolved in MeOH and a precipitate is formed upon standing. The mixture is filtered to give the title compound as a beige solid: ES-MS 437 (M+H$^+$); single peak at $t_R$=17.8 min (System 4); $R_f$=0.2 (1:20, MeOH/CH$_2$Cl$_2$, followed by 1:10, MeOH/CH$_2$Cl$_2$).

Example 49

[4-(3-Benzo[1,3]dioxol-5-yl-1H-pyrazol-4-yl)-pyrimidin-2-yl]-3-methylsulfanyl-phenyl)-amine n-Butyl lithium (1.6 M in hexane, 2.28 mL, 3.65 mmol) is dropwise added to 3-(methylthio)aniline (0.58 mL, 3.69 mmol) in THF (anhydrous, 10 mL) at −78° C. and stirred for 1 h. Sulfoxide-B (404.2 mg, 1.23 mmol) in THF (anhydrous, 20 mL) is added. The reaction mixture is allowed to warm to rt, stirred for 41 h, and quenched with H$_2$O. The crude product is extracted with EtOAc. The organic layer is washed with saturated NaCl (aq.), dried over MgSO$_4$, filtered, concentrated, and chromatographed on SiO$_2$ (linear gradient 50→60% EtOAc in Hexane) to obtain the title compound as an off-white solid: ES-MS 404.3 (M+H)$^+$; single peak at $t_R$=16.264 min (System 5); $R_f$=0.17 (50% EtOAc/Hexane).

Example 50

{4-[3-(2,3-Dimethyl-phenyl)-1H-pyrazol-4-yl]-pyrimidin-2-yl}-[4-(4-methyl-piperazin-1-yl)phenyl]-amine The title compound is prepared as described in Example 33 using 2,3-dimethyl-benzoic acid ethyl ester.

2,3-Dimethylbenzoic acid ethyl ester is prepared from 2,3-dimethylbenzoic acid (98% Lancaster) as described in Example 5.

Example 51

{4-[3-(2,3-Dimethyl-phenyl)-1H-pyrazol-4-yl]-pyrimidin-2-yl}-(3,4,5-trimethoxy-phenyl)-amine The title compound is prepared as described in Example 33 using 2,3-dimethyl-benzoic acid ethyl ester (see Example 50) and 3,4,5-trimethoxyphenylamine.

Example 52

{4-[3-(2-Chloro-phenyl)-1H-pyrazol-4-yl]-pyrimidin-2-yl}-[4-(4-methyl-piperazin-1-yl)-phenyl]-amine The title compound is prepared as described in Example 33 using ethyl 2-chlorobenzoate (98% Lancaster).

Example 53

{4-[3-(2-Chloro-phenyl)-1H-pyrazol-4-yl]-pyrimidin-2-yl}-(3,4,5-trimethoxy-phenyl)-amine The title compound is prepared as described in Example 33 using ethyl 2chlorobenzoate (98% Lancaster) and 3,4,5-trimethoxyphenylamine.

General Synthetic Scheme 5:

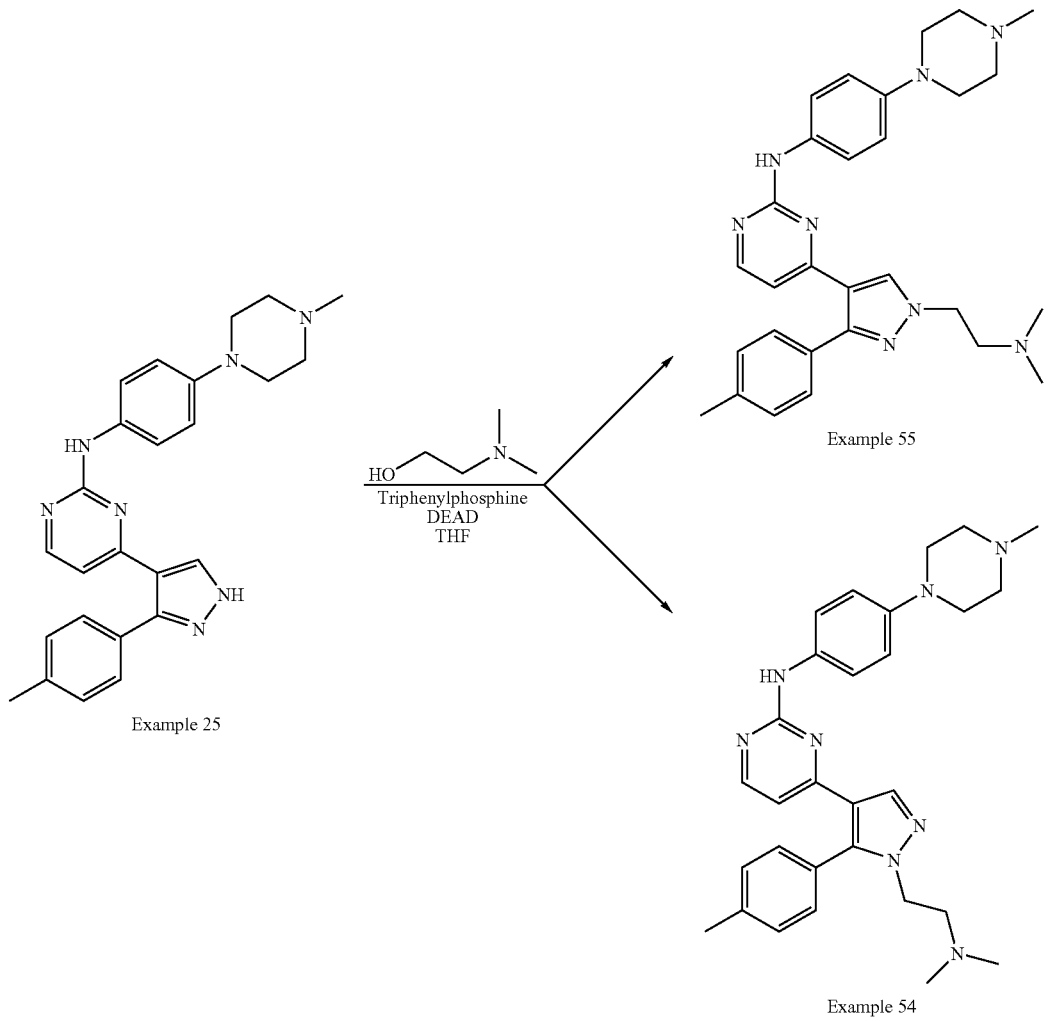

Example 54

{4-[1-(2-Dimethylamino-ethyl)-5-p-tolyl-1H-pyrazol-4-yl]-pyrimidin-2-yl}-[4-(4-methyl-piperazin-1-yl)-phenyl]-amine To the suspension of 90 mg (0.211 mMol) of [4-(4-methyl-piperazin-1-yl)-phenyl]-[4-(3-p-tolyl-1H-pyrazol-4-yl)-pyrimidin-2-yl]-amine (Example 25) in 4.5 mL of THF is added 38 mg (0.426 mMol) of 2-dimethylamino-ethanol (Fluka) and 122 mg (0.465 mMol) of triphenylphosphine (Fluka). The yellowish suspension is cooled to 0° C. and treated with 81 mg (0.465 mMol) of DEAD*. The mixture is stirred without cooling for 17 h, followed by heating for 24 h at 60° C. After cooling to rt, the reaction mixture is filtered and washed with 5 mL of THF. The filtrate is concentrated under reduced pressure and the crude product is purified by repeated chromatography on silica gel, eluting with $CH_2Cl_2$/MeOH (9:1) and $CH_2Cl_2$/MeOH/$H_2O$ 70:30:5 to obtain the title compound as beige crystals.

* Literature: Mitsunobu, Oyo; Synthesis 1981, p. 1-27.

Example 55

{4-[1-(2-Dimethylamino-ethyl)-3-p-tolyl-1H-pyrazol-4-yl]-pyrimidin-2-yl}-[4-(4-methyl-piperazin-1-yl)-phenyl]-amine The title compound is prepared as described in Example 54 and isolated from the same reaction mixture.

General Synthetic Scheme 6:

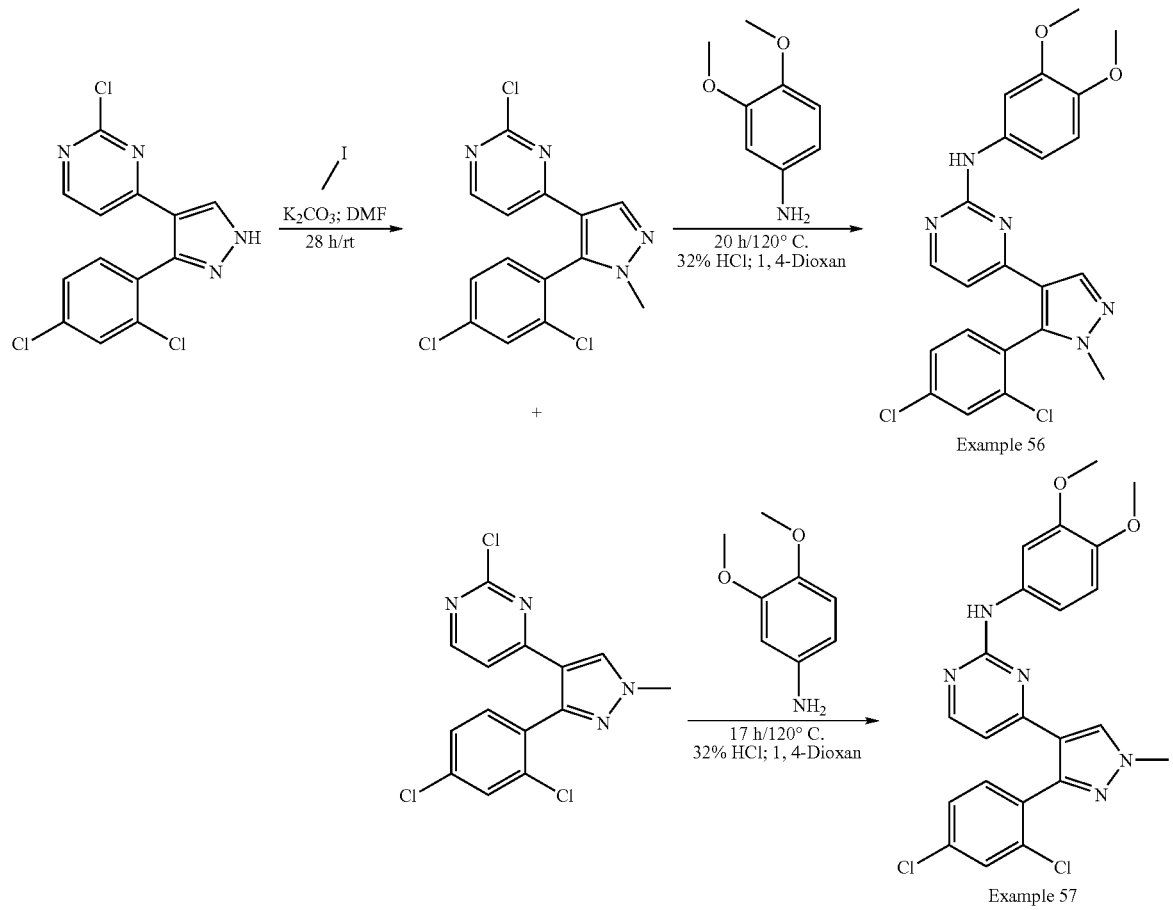

Example 56

{4-[5-(2,4-Dichloro-phenyl)-1-methyl-1H-pyrazol-4-yl]-pyrimidin-2-yl}-(3,4-dimethoxy-phenyl)-amine The title compound is prepared as described in Example 1 but using 2-chloro[5-(2,4-dichloro-phenyl)-1-methyl-1H-pyrazol-4-yl]-pyrimidine and 3,4-dimethoxy-phenylamine.

2-Chloro-4-[5-(2,4dichloro-phenyl)-1-methyl-1H-pyrazol-4-yl]-pyrimidine:

To the solution of 1 g (3.07 mMol) of 2-chloro-4-[3-(2,4-dichloro-phenyl)-1H-pyrazol-4-yl]-pyrimidine in 10 mL of DMF is added 0.467 g (3.38 mMol) of potassium carbonate at rt under an atmosphere of Argon. After stirring for 30 min, 1.15 mL (18.42 mMol) of methyl iodide is added. After completion of the reaction (28 h), the mixture is poured onto 100 mL of water, and extracted repeatedly with ethyl acetate. The combined organic layers are washed with NaHCO$_3$, water, brine, dried (Na$_2$SO$_4$), filtered and concentrated under reduced pressure. The crude product is purified twice over silica gel, eluting with ethyl acetate/hexanes (1:1) and CH$_2$Cl$_2$/MeOH (99:1) to obtain the title compound as orange crystals; m.p. 122-125° C.; TLC (silica gel) R$_f$=0.19 (CH$_2$Cl$_2$/MeOH 99:1).

2-Chloro-4-[3-(2,4-dichloro-phenyl)-1H-pyrazol-4-yl]-pyrimidine is prepared as described in Example 1 using 2,4-dichloro-benzoic acid ethyl ester m.p. 83-90° C.; TLC (silica gel) R$_f$=0.28 (ethyl acetate/hexane 1:1).

Example 57

{4-[3-(2,4Dichloro-phenyl)-1-methyl-1H-pyrazol-4-yl]-pyrimidin-2-yl}-(3,4-dimethoxy-phenyl)-amine The title compound is prepared as described in Example 1 but using 2-chloro-4-[3-(2,4-dichloro-phenyl)-1-methyl-1H-pyrazol-4-yl]-pyrimidine and 3,4-dimethoxy-phenylamine.

2-Chloro-4-[3-(2,4-dichloro-phenyl)-1-methyl-1H-pyrazol-4-yl]pyrimidine:

The title compound is prepared as described in Example 56 for 2-chloro[5-(2,4-dichloro-phenyl)-1-methyl-1H-pyrazol-4-yl]-pyrimidine and isolated from the same reaction mixture as yellow-orange crystals; m.p. 165-166° C.; TLC (silica gel) R$_f$=0.38 (CH$_2$Cl$_2$/MeOH 99:1).

Example 58

4-[4-(3-p-Tolyl-1H-pyrazol-4-yl)-pyrimidin-2-ylamino]-benzoic acid

The title compound is prepared as described in Example 30 using 4-methyl-benzoic acid ethyl ester.

Example 59

(4Methyl-piperazin-1-yl)-{4-[4-(3-p-tolyl-1H-pyrazol-4-yl)-pyrimidin-2-ylamino]-phenyl}-methanone The title compound is prepared as described in Example 31 using 4-[4(3-p-tolyl-1H-pyrazol-4-yl)-pyrimidin-2-ylamino]-benzoic acid (Example 58).

Example 60

[4-(4-Methyl-piperazin-1-ylmethyl)-phenyl]-[4-(3-p-tolyl-1H-pyrazol-4-yl)-pyrimidin-2-yl]-amine The title compound is prepared as described in Example 32 using (4-methyl-piperazin-1-yl)-{4-[4-(3-p-tolyl-1H-pyrazol-4-yl)-pyrimidin-2-ylamino]-phenyl}-methanone (Example 59).

Example 61

{4-[3-(4-Chloro-phenyl)-1-(2-dimethylamino-ethyl)-1H-pyrazol-4-yl]-pyrimidin-2-yl-}4-[4-(4-methyl-piperazin-1-yl)-phenyl]1-amine The title compound is prepared as described in Example 55 using 4-chloro-benzoic acid ethyl ester.

Example 62

{4-[5-(4-Chloro-phenyl)-1-(2-dimethylamino-ethyl)-1H-pyrazol-4-yl]-pyrimidin-2-yl}-4-[4-(4-methyl-piperazin-1-yl)-phenyl]-amine The title compound is prepared as described in Example 54 using 4-chloro-benzoic acid ethyl ester.

Example 63

[4-(4-Methyl-piperazin-1-yl)-phenyl]-[4-(1-methyl-5-p-tolyl-1H-pyrazol-4-yl)-pyrimidin-2-yl]-amine The title compound is prepared as described in Example 54 using methanol instead.

Example 64

[4-(4-Methyl-piperazin-1-yl)-phenyl]-[4-(1-methyl-3-p-tolyl-1H-pyrazol-4-yl)-pyrimidin-2-yl]-amine The title compound is prepared as described in Example 55 using methanol.

Example 65

[4-(4-Methyl-piperazin-1-ylmethyl)-phenyl]-[4(1-methyl-5-p-tolyl-1H-pyrazol-4-yl)-pyrimidin-2-yl]-amine The title compound is prepared as described in Example 54 starting from [4-(4-methyl-piperazin-1-ylmethyl)-phenyl]-[4-(3-p-tolyl-1H-pyrazol-4-yl)-pyrimidin-2-yl]-amine (Example 60) and methanol.

Example 66

[4-(4-Methyl-piperazin-1-ylmethyl)-phenyl]-[4-(1-methyl-3-p-tolyl-1H-pyrazol-4-yl)-pyrimidin-2-yl]-amine The title compound is prepared as described in Example 55 starting from [4(4methyl-piperazin-1-ylmethyl)-phenyl]-[4-(3-p-tolyl-1H-pyrazol-4-yl)-pyrimidin-2-yl]-amine (Example 60) and methanol.

Example 67

{4-[3-(4-Chloro-phenyl)-1H-pyrazol-4-yl]-pyrimidin-2-yl}-(3,4,5-trimethoxy-phenyl)-amine The title compound is prepared as described in Example 1 using 3,4,5-trimethoxyphenylamine.

Example 68

{4-[3-(4-Chloro-phenyl)-1H-pyrazol-4yl]-pyrimidin-2-yl}-(3,4-dimethoxy-phenyl)-amine The title compound is prepared as described in Example 1 using 3,4dimethoxy-phenylamine.

Example 69

{4-[3-(4-Chloro-phenyl)-1H-pyrazol-4-yl]-pyrimidin-2-yl}-(3-methoxy-phenyl)-amine The title compound is prepared as described in Example 1 using 4methoxy-phenylamine.

Example 70

{4-[3-(4-Chloro-phenyl)-1-(2-dimethylamino-ethyl)-1H-pyrazol-4-yl]-pyrimidin-2-yl}-(3,4,5-trimethoxy-phenyl)-amine The title compound is prepared as described in Example 55 starting from {4-[3-(4-chloro-phenyl)-1H-pyrazol-4-yl]pyrimidin-2-yl}-(3,4,5-trimethoxy-phenyl)-amine (Example 67).

Example 71

{4-[5-(4-Chloro-phenyl)-1-(2-dimethylamino-ethyl)-1H-pyrazol-4-yl]-pyrimidin-2-yl}-(3,4,5-trimethoxy-phenyl)-amine The title compound is prepared as described in Example 54 starting from {4-[3-(4-chloro-phenyl)-1H-pyrazol-4-yl]-pyrimidin-2-yl}-(3,4,5-trimethoxy-phenyl)-amine (Example 67).

Example 72

{4-[5-(4-Chloro-phenyl)-1-(2-dimethylamino-ethyl)-1H-pyrazol-4yl]-pyrimidin-2-yl}-(3,4,5-trimethoxy-phenyl)-amine The title compound is prepared as described in Example 55 starting from {4-[3-(4-chloro-phenyl)-1H-pyrazol-4-yl]-pyrimidin-2-yl}-(3,4-dimethoxy-phenyl)-amine (Example 68).

Example 73

{4-[5-(4-Chloro-phenyl)-1-(2-dimethylamino-ethyl)-1H-pyrazol-4-yl]-pyrimidin-2-yl}-(3,4-dimethoxy-phenyl)-amine The title compound is prepared as described in Example 54, starting from {4-[3-(4-chloro-phenyl)-1H-pyrazol-4-yl]-pyrimidin-2-yl}-(3,4-dimethoxy-phenyl)-amine (Example 68).

Example 74

{4-[3-(4Chloro-phenyl)-1-(2-dimethylamino-ethyl)-1H-pyrazol-4-yl]-pyrimidin-2-yl}-(3-methoxy-phenyl)-amine The title compound is prepared as described in Example 55 starting from {4-[3-(4chloro-phenyl)-1H-pyrazol-4-yl]-pyrimidin-2-yl}-(3-methoxy-phenyl)-amine (Example 69).

Example 75

{-4-[5-(4Chloro-phenyl)-1-(2-dimethylamino-ethyl)-1H-pyrazol-4-yl]-pyrimidin-2-yl}-(3-methoxy-phenyl)-amine The title compound is prepared as described in Example 54 starting from {4-[3-(4-chloro-phenyl)-1H-pyrazol-4-yl]-pyrimidin-2-yl}-(3-methoxy-phenyl)-amine (Example 69).

Example 76

{4-[3-(4-Chloro-phenyl)-1-(2-dimethylamino-ethyl)-1H-pyrazol-4-yl]-pyrimidin-2-yl}-[4-(4-methyl-piperazin-1-ylmethyl)-phenyl]-amine The title compound is prepared as described in Example 55, starting from {4-[3-(4-chloro-phenyl)1H-pyrazol-4-yl]-pyrimidin-2-yl}-[4-(4-methyl-piperazin-1-yl-methyl)-phenyl]-amine (Example 32) and 2-dimethylamino-ethanol (Fluka).

Example 77

{4-[5-(4-Chloro-phenyl)-1-(2-dimethylamino-ethyl)-1H-pyrazol-4yl]-pyrimidin-2-yl}-[4-(4-methyl-piperazin-1-ylmethyl)-phenyl]-amine The title compound is prepared as described in Example 54, starting from {4-[3-(4-chloro-phenyl)-1H-pyrazol-4-yl]-pyrimidin-2-yl}-[4-(4-methyl-piperazin-1-yl-methyl)-phenyl]-amine (Example 32) and 2-dimethylamino-ethanol (Fluka).

Example 78

{4-[3-(4-Chloro-phenyl)-1-methyl-1H-pyrazol-4yl]-pyrimidin-2-yl}-[4-(4-methyl-piperazin-1-ylmethyl)-phenyl]-amine The title compound is prepared as described in Example 55 starting from {4-[3-(4chloro-phenyl)-1H-pyrazol-4-yl]-pyrimidin-2-yl}-[4-(4-methyl-piperazin-1-yl-methyl-phenyl]-amine (Example 32) and methanol.

Example 79

{4-[5-(4Chloro-phenyl)-1-methyl-1H-pyrazol-4-yl]-pyrimidin-2-yl}-[4-(4-methyl-piperazin-1-ylmethyl)-phenyl]-amine The title compound is prepared as described in Example 54 starting from {4-[3-(4-chloro-phenyl)-1H-pyrazol-4-yl]-pyrimidin-2-yl)}-[4-(4-methyl-piperazin-1-yl-methyl)-phenyl]-amine (Example 32) and methanol.

Example 80

{4-[3-(4-Chloro-phenyl)-1-(1-methyl-piperidin-4-yl)-1H-pyrazol-4yl]-pyrimidin-2-yl}-[4-(4-methyl-piperazin-1-yl-methyl)-phenyl]-amine The title compound is prepared as described in Example 55 starting from {4-[3-(4chloro-phenyl)-1H-pyrazol-4-yl]-pyrimidin-2-yl}-[4-(4-methyl-piperazin-1-yl-methyl)-phenyl]-amine (Example 32) and 1-methyl-piperidin-4-ol.

Example 81

{4-[5-(4-Chloro-phenyl)-1-(1-methyl-piperidin-4yl)-1H-pyrazol-4yl]-pyrimidin-2-yl}-[4-(4methyl-piperazin-1-ylmethyl)-phenyl]-amine The title compound is prepared as described in Example 54 starting from {4-[3-(4-chloro-phenyl)-1H-pyrazol-4yl]-pyrimidin-2-yl}-[4-(4-methyl-piperazin-1-yl-methyl)-phenyl]-amine (Example 32) and 1-methyl-piperidin-4-ol.

Example 82

{4-[1-(2-Dimethylamino-ethyl)-5-p-tolyl-1H-pyrazol-4-yl]-pyrimidin-2-yl}-[4-(4 methyl-piperazin-1-ylmethyl)-phenyl]-amine The title compound is prepared as described in Example 54 starting from [4-(4-methyl-piperazin-1-ylmethyl)-phenyl]-[4-3-p-tolyl-1H-pyrazol-4-yl)-pyrimidin-2-yl]-amine (Example 60) and 2-dimethylamino-ethanol.

Example 83

{4-[1-(2-Dimethylamino-ethyl)-3-p-tolyl-1H-pyrazol-4-yl]-pyrimidin-2-yl}-[4-(4-methyl-piperazin-1-ylmethyl)-phenyl]-amine The title compound is prepared as described in Example 55 starting from [4-(4-methyl-piperazin-1-ylmethyl)-phenyl]-[4-(3-p-tolyl-1H-pyrazol-4-yl)-pyrimidin-2-yl]-amine (Example 60) and 2-dimethylamino-ethanol.

Example 84

[4-(4-Methyl-piperazin-1-ylmethyl)-phenyl]-{4-[1-(1-methyl-piperidin-4-yl)-5-p-tolyl-1H-pyrazol-4-yl]-pyrimidin-2-yl}-amine The title compound is prepared as described in Example 54 starting from [4-(4-methyl-piperazin-1-ylmethyl)-phenyl]-[4-(3-p-tolyl-1H-pyrazol-4-yl)-pyrimidin-2-yl]-amine (Example 60 and 1-methyl-piperidin-4-ol.

Example 85

[4-(4-Methyl-piperazin-1-ylmethyl)-phenyl]-{4-[1-(1-methyl-piperidin-4-yl)-3-p-tolyl-1H-pyrazol-4-yl]-pyrimidin-2-yl}-amine The title compound is prepared as described in Example 55 starting from [4-(4-methyl-piperazin-1-ylmethyl)-phenyl]-[4-(3-p-tolyl-1H-pyrazol-4-yl)-pyrimidin-2-yl]-amine (Example 60) and 1-methyl-piperidin-4-ol.

Physical Characterization: data Examples 50-85

| Example No. | m.p. from to [° C.] | | HPLC [min.]/ System 1 | mass spectra; ESI; m/z = [M + H]+ |
|---|---|---|---|---|
| 50 | 305 | 307 | 3.48 | |
| 51 | 249 | 250 | 4.78 | |
| 52 | 310 | 315 | 3.18 | |
| 53 | 257.5 | 259.5 | 4.43 | |
| 54 | 184 | 187 | 2.60 | |
| 55 | 174 | 176 | 2.86 | |
| 56 | 157 | 159 | 5.04 | |
| 57 | 180 | 182 | 5.01 | |
| 58 | 341 | 355 | 4.16 | |
| 59 | 264 | 266 | 3.29 | |
| 60 | 250 | 253 | 3.17 | |
| 61 | 148 | 156 | 2.93 | |
| 62 | 173 | 179 | 2.64 | |
| 63 | 261 | 263 | 3.65 | |
| 64 | 203 | 206 | 3.52 | |
| 65 | 192 | 193 | 3.6 | |
| 66 | 151 | 153 | 3.47 | |
| 67 | 271 | 277 | 4.67 | |
| 68 | 261 | 265 | 4.28 | |
| 69 | 261 | 264 | 4.98 | |
| 70 | 150 | 153 | 4.15 | |
| 71 | 153 | 160 | 3.86 | |
| 72 | amorphous | | 3.81 | 479.1 |
| 73 | 157 | 160 | 3.54 | |
| 74 | amorphous | | 4.45 | 449 |
| 75 | 118 | 125 | 4.20 | |
| 76 | amorphous | | 2.90 | 531.2 |
| 77 | 159 | 163 | 2.68 | |
| 78 | 166 | 169 | 3.51 | |
| 79 | 186 | 189 | 3.59 | |
| 80 | 164 | 166 | 2.94 | |
| 81 | 180 | 182 | 2.86 | |
| 82 | 123 | 147 | 2.68 | |
| 83 | 62 | 66 | 2.88 | |
| 84 | 187 | 188 | 2.80 | |
| 85 | 174 | 175 | 2.93 | |

Example 86

{4-[3-(4-Chloro-3-methyl-phenyl)-1H-pyrazol-4yl]-pyrimidin-2-yl}-(3,4-dimethoxy-phenyl)-amine The title compound is prepared as described in Example 1 using 4-chloro-3-methyl-benzoic acid ethyl ester and 3,4-dimethoxy-phenylamine instead.

Example 87

(3-Methoxy-phenyl)-{4-[3-(4trifluoromethyl-phenyl)-1H-pyrazol-4-yl]-pyrimidin-2-yl}-amine The title compound is prepared as described in Example 1 using 4-trifluoromethyl-benzoic acid ethyl ester and 3-methoxy-phenylamine instead.

Example 88

(3-Methoxy-phenyl)-{4-[1-methyl-3-(4-trifluoromethyl-phenyl)-1H-pyrazol-4-yl]-pyrimidin-2-yl}-amine The title compound is prepared as described in Example 55 starting from (3-methoxy-phenyl)-{4-[3-(4-trifluoromethyl-phenyl)-1H-pyrazol-4yl]-pyrimidin-2-yl}-amine (Example 87) and using methanol instead.

Example 89

(3-Methoxy-phenyl)-{4-[1-methyl-5-(4-trifluoromethyl-phenyl)-1H-pyrazol-4-yl]-pyrimidin-2-yl}-amine The title compound is prepared as described in Example 88 and isolated from the same reaction mixture.

Example 90

{4-[1-(2-Dimethylamino-ethyl)-3-(4-trifluoromethyl-phenyl)-1H-pyrazol-4-yl]-pyrimidin-2-yl}-(3-methoxy-phenyl)-amine The title compound is prepared as described in Example 55 starting from (3-methoxy-phenyl)-{4-[3-(4-trifluoromethyl-phenyl)-1H-pyrazol-4-yl]-pyrimidin-2-yl}-amine (Example 87).

Example 91

{4-[3-(4-Chloro-phenyl)1-methyl-1H-pyrazol-4yl]-pyrimidin-2-yl}-[4-(4-methyl-piperazin-1-yl)-phenyl]-amine The title compound is prepared as described in Example 55 starting from {4-[3-(4-chloro-phenyl)-1H-pyrazol-4-yl]-pyrimidin-2-yl}-[4-(4-methyl-piperazin-1-yl)-phenyl]-amine (Example 1) and using methanol instead.

Example 92

{4-[5-(4-Chloro-phenyl)-1-methyl-1H-pyrazol-4-yl]-pyrimidin-2-yl}-[4-(4methyl-piperazin-1-yl)-phenyl]-amine The title compound is prepared as described in Example 91 and isolated from the same reaction mixture.

Example 93

[4-(4-Methyl-piperazin-1-yl)-phenyl]-{4-[3-(4trifluoromethyl-phenyl)-1H-pyrazol-4-yl]-pyrimidin-2-yl}-amine The title compound is prepared as described in Example 1 using 4-trifluoromethyl-benzoic acid ethyl ester instead.

Example 94

[4-(4-Methyl-piperazin-1-ylmethyl)-phenyl]-{4-[3-(4-trifluoromethyl-phenyl)-1H-pyrazol-4-yl]-pyrimidin-2-yl}-amine The title compound is prepared as described in Examples 30-32 using 4-trifluoromethyl-benzoic acid ethyl ester instead.

Example 95

[4-(3-p-Tolyl-1H-pyrazol-4-yl)-pyrimidin-2-yl]-(3-trifluoromethoxy-phenyl)-amine The title compound is prepared as described in Example 1 using 4-methyl-benzoic acid ethyl ester and 3-trifluoromethoxy-phenylamine instead.

Example 96

(4-Methanesulfonyl-phenyl)-[4-(3-p-tolyl-1H-pyrazol-4-yl)-pyrimidin-2-yl]-amine

The title compound is prepared as described in Example 1 using 4-methyl-benzoic acid ethyl ester and 4-methyl-benzoic acid ethyl ester instead.

Example 97

(3-{4-[3-(4-Chloro-phenyl)-1H-pyrazol-4-yl]-pyrimidin-2-ylamino}-phenyl)-(4-methyl-piperazin-1-yl)-methanone The title compound is prepared as described in Examples 30-31 using 3-amino-benzoic acid instead.

Example 98

{4-[3-(4Chloro-phenyl)-1H-pyrazol-4yl]-pyrimidin-2-yl}-(4-methane-sulfonyl-phenyl)-amine The title compound is prepared as described in Example 96 using 4-chloro-benzoic acid ethyl ester instead.

Example 99

{(3-Methoxy-phenyl)-[4-(3-p-tolyl-1H-pyrazol-4-yl)-pyrimidin-2-yl]-amine

The title compound is prepared as described in Example 1 using 4-methyl-benzoic acid ethyl ester and 3-methoxy-phenylamine instead.

Example 100

(3-Methoxy-phenyl)-{4-[3-(3-trifluoromethyl-phenyl)-1H-pyrazol-4-yl]-pyrimidin-2-yl}-amine The title compound is prepared as described in Example 1 using 3-trifluoromethyl-benzoic acid ethyl ester and 3-methoxy-phenylamine instead.

Example 101

[4-(4-Ethyl-piperazin-1-ylmethyl)-phenyl]-[4-(3-p-tolyl-1H-pyrazol-4)-pyrimidin-2-yl]-amine The title compound is prepared as described in Examples 58-60 using 1-ethyl-piperazine instead.

Example 102

[3-(4-Methyl-piperazin-1-ylmethyl)-phenyl]-[4-(3-p-tolyl-1H-pyrazol-4-yl)-pyrimidin-2-yl]-amine The title compound is prepared as described in Examples 58-60 using 3-amino-benzoic acid instead.

Example 103

{4-[3-(4-Chloro-phenyl)-1H-pyrazol-4-yl]-pyrimidin-2-yl}-[3-(4-methyl-piperazin-1-ylmethyl)-phenyl]-amine The title compound is prepared as described in Examples 58-60 using 4-chloro-benzoic acid ethyl ester and 3-amino-benzoic acid instead.

Example 104

[3-(4-Methyl-piperazin-1-ylmethyl)-phenyl]-[4-(3-phenyl-1H-pyrazol-4-yl)-pyrimidin-2-yl]-amine The title compound is prepared as described in Example 103. De-chlorination took place due to prolonged exposure to lithium aluminum hydride.

Example 105

{4-[3-(4-Chloro-phenyl)-1-methyl-1H-pyrazol-4-yl]-pyrimidin-2-yl}-[3-(4-methyl-piperazin-1-ylmethyl)-phenyl]-amine The title compound is prepared as described in Example 88 starting from {4-[3-(4-chloro-phenyl)-1H-pyrazol-4-yl]-pyrimidin-2-yl}-[3(4-methyl-piperazin-1-yl-methyl)-phenyl]-amine Example 103).

Example 106

{4-[5-(4-Chloro-phenyl)-1-methyl-1-H-pyrazol-4yl]-pyrimidin-2-yl}-[3-(4-methyl-piperazin-1-ylmethyl)-phenyl]-amine The title compound is prepared as described in Example 105 and isolated from the same reaction mixture.

| Physical Characterization: data Examples 86-106 | | | |
|---|---|---|---|
| Example No. | m.p. from to [° C.] | | HPLC [min.]/ System 1 | mass spectra; ESI; m/z = [M + H]⁺ |
| 86 | | | 4.54 | 422.1 |
| 87 | 260 | 275 | 5.34 | |
| 88 | 173 | 174 | 5.96 | |
| 89 | 167 | 168 | 5.81 | |
| 90 | 111 | 115 | 4.72 | |
| 91 | 202 | 204 | 3.56 | |
| 92 | 264 | 267 | 3.64 | |
| 93 | 276 | 280 | 3.60 | |
| 94 | 228 | 235 | 3.56 | |
| 95 | 283 | 284 | 6.25 | |
| 96 | 305 | 307 | 4.59 | |
| 97 | 338 | 343 | 3.47 | |
| 98 | 293 | 296 | 4.76 | |
| 99 | 266 | 273 | 4.83 | |
| 100 | 208 | 220 | 5.29 | |
| 101 | 257 | 259 | 3.21 | |
| 102 | 239 | 241 | 3.21 | |
| 103 | 243 | 248 | 3.31 | |
| 104 | 245 | 248 | 2.92 | |
| 105 | 152 | 157 | 3.64 | |
| 106 | 125 | 130 | 3.71 | |

Example 107

{4-[3-(4-Chloro-phenyl)-1-(1methyl-piperidin-4-ylmethyl)-1H-pyrazol-4-yl]-pyrimidin-2-yl}-(3-methoxy-phenyl)-amine The title compound is prepared as described in Example 55 using 3-methoxy-phenylamine and 1-methyl-4-piperidinemethanol (Chem Pacific; 33077; for preparation see also Example 27).

Example 108

{4-[5-(4-Chloro-phenyl)-1-(1-methyl-piperidin-4-ylmethyl)-1H-pyrazol-4-yl]-pyrimidin-2-yl}-(3-methoxy-phenyl)-amine The title compound is prepared as described in Example 107 and isolated from the same reaction mixture.

Example 109

[4-(4-Ethyl-piperazin-1-yl)-phenyl]-[4-(3-p-tolyl-1H-pyrazol-4yl)-pyrimidin-2-yl]-amine The title compound is prepared as described in Example 1 using 4-methyl-benzoic acid ethyl ester and 4-(4-ethyl-piperazin-1-yl)-phenylamine instead.
4-(4-Ethyl-piperazin-1-yl)-phenylamine is prepared in 2 steps from 1-bromo-4-nitro-benzene and 1-ethyl-piperazine as described in Example 1, Step A and B.

Example 110

[4-(4-Methyl-piperazin-1-ylmethyl)-phenyl]-{4-[3-(3-trifluoromethyl-phenyl)-1H-pyrazol-4yl]-pyrimidin-2-yl}-amine The title compound is prepared as described in Examples 30-32 using 3-trifluoromethyl-benzoic acid ethyl ester instead.

Example 111

2-(4-{4-[4-(3-p-Tolyl-1H-pyrazol-4yl)-pyrimidin-2-ylamino]-benzyl}piperazin-1-yl)-ethanol The title compound is prepared as described in Examples 58-60 using 2-piperazin-1-yl-ethanol instead.

Example 112

{4-[3-(4-Chloro-phenyl)-1-methyl-1H-pyrazol-4-yl]-pyrimidin-2-yl}-[3-(1-methyl-piperidin-4-ylmethoxy)-phenyl]-amine The title compound is prepared as described in Example 91 using 3-(1-methyl-piperidin-4-ylmethoxy)-phenylamine instead.
For the preparation of 3-(1-methyl-piperidin-4-ylmethoxy)-phenylamine see Example 125.

Example 113

3-{4-[3-(3,5-Dimethoxy-phenyl)-1H-pyrazol-4-yl]-pyrimidin-2-ylamino}-benzenesulfonamide The title compound is prepared as described in Example 1 using 3,5-dimethoxy-benzoic acid ethyl ester and 3-aminobenzenesulfonamide.

Example 114

{4-[3-(4-Chloro-phenyl)-1H-pyrazol-4yl]-pyrimidin-2-yl}-[4-(4-ethyl-piperazin-1-ylmethyl)-phenyl]-amine The title compound is prepared as described in Example 32 using 1-ethyl-piperazine instead.

Example 115

[4-(4-Ethyl-piperazin-1-ylmethyl)-phenyl]-[4-(3-phenyl-1H-pyrazol-4-yl)-pyrimidin-2-yl]-amine The title compound is prepared as described in Example 114. De-chlorination took place due to prolonged exposure to lithium aluminum hydride.

Example 116

{4-[3-(4-Chloro-phenyl)-1H-pyrazol-4-yl]-pyrimidin-2-yl}-[4-(1H-tetrazol-5-yl)-phenyl]-amine The title compound is prepared starting from 4-{4-[3-(4-chloro-phenyl)-1H-pyrazol-4-yl]-pyrimidin-2-ylamino}-benzonitrile. 4-{4-[3-(4-chloro-phenyl)-1H-pyrazol-4-yl]-pyrimidin-2-ylamino}-benzonitrile (0.932 g; 2.5 mMol) is suspended in o-xylene (10 mL) and treated at rt with azidotributyltin (1.66 g; 1.37 mL; 5 mMol). After stirring the yellow suspension at 160° C. for 117 h the reaction mixture is filtered off without cooling and the crystals are washed with o-xylene. Since the reaction is still incomplete, the crude product is resuspended in o-xylene (20 mL) and treated at rt with azidotributyltin (1.37 mL; 5 mMol). After stirring the yellow suspension at 160° C. for 117 h the reaction mixture is filtered off without cooling and the crystals are washed with o-xylene. The crude product is suspended in methanol (1.00 mL), refluxed and filtered without cooling. The crude product is acidified with 4N HCL/methanol and extracted with ethyl acetate. The aqueous layer is basified with 4N NaOH (ca. pH 12) and extracted with ethyl acetate. Upon this treatment, the product precipitates from the aqueous layer and is filtered off to obtain the title compound.

4-{4[3-(4-Chloro-phenyl)-1H-pyrazol-4-yl]-pyrimidin-2-ylamino}-benzonitrile:
The title compound is prepared as described in Example 1 using 4-aminobenzonitrile HCl salt instead.

Example 117

[4-(4-Ethyl-piperazin-1-ylmethyl)-phenyl]-[4-(1-methyl-3-p-tolyl-1H-pyrazol-4-yl)-pyrimidin-2-yl]-amine

[4-(4-Ethyl-piperazin-1-ylmethyl)-phenyl]-[4-(3-p-tolyl-1H-pyrazol-4-yl)-pyrimidin-2-yl]-amine (Example 101) (165 mg; 0.364 mMol) is suspendend in toluene (3 mL) and treated with DMF-DMA (168 mg; 1.32 mMol, 187 μL) at rt. The mixture is stirred at reflux for a total of 102 h whereby additional DMF-DMA is added after 48 h (187 μL), after 61 h (187 μL) and after 82 h (374 μL). Upon completion of the reaction and cooling to rt the solvent is removed under reduced pressure. The crude product mixture is purified by reversed phase chromatography (Lichroprep® RP18 15-25 μM; eluting with 18% CH₃CN (0.1% TFA)/82% H₂O (0.1% TFA)). The pure fractions 27-34 are combined and evaporated. The residue is dissolved in H₂O (2 mL) and neutralized with 1N NaOH. The crystalline product (free base) is filtered off, washed with H₂O and dried at 60° C. to obtain the title compound as beige crystalline powder.

Example 118

[4-(4-Ethyl-piperazin-1-ylmethyl)-phenyl]-[4-(1-methyl-5-p-tolyl-1H-pyrazol-4-yl)-pyrimidin-2-yl]-amine The title compound is isolated from the reaction described in Example 117. The pure fractions 40-59 are combined and evaporated. The residue is dissolved in H$_2$O (2 mL) and neutralized with 1N NaOH. The crystalline product (free base) is filtered off, washed with H$_2$O and dried at 60° C. to obtain the title compound as beige crystalline powder.

Example 119

{4-[3-(4-Chloro-phenyl)-1H-pyrazol-4-yl]-pyrimidin-2-yl}-{4-[(2,2,6,6-tetramethyl-piperidin-4-ylamino)-methyl]-phenyl}-amine The title compound is prepared as described in Example 32 using 2,2,6,6tetramethyl-piperidin-4-ylamine instead.

Example 120

[4(3-Phenyl-1H-pyrazol-4-yl)-pyrimidin-2-yl]-{4[(2,2,6,6-tetramethyl-piperidin-4-ylamino)-methyl]-phenyl}-amine The title compound is prepared as described in Example 119. De-chlorination took place due to prolonged exposure to lithium aluminum hydride.

Example 121

{4-[3-(4-Chloro-phenyl)-1H-pyrazol-4yl]-pyrimidin-2-yl}-[4-(4-ethyl-piperazin-1-yl)-phenyl]-amine The title compound is prepared as described in Example 109 using 4-chloro-benzoic acid ethyl ester instead.

Example 122

{4-[3-(4-Chloro-phenyl)-1H-pyrazol-4yl]-pyrimidin-2-yl}-(4piperazin-1-yl-phenyl)-amine The title compound is prepared as described in Example 1 using piperazine instead.

Physical Characterization: data Examples 107-122

| Example No. | m.p. from to [° C.] | | HPLC [min.]/System [R1] | mass spectra; ESI; m/z = [M + H]$^+$ |
|---|---|---|---|---|
| 107 | 65 | 68 | 4.44 | |
| 108 | 180 | 182 | 4.21 | |
| 109 | 280 | 282 | 3.27 | |
| 110 | 221 | 223 | 3.45 | |
| 111 | 233 | 240 | 3.37 | |
| 112 | 138 | 141 | 4.51 | |
| 113 | 257 | 259 | 4.27 | |
| 114 | 247 | 253 | 3.48 | |
| 115 | 227 | 233 | 3.14 | |
| 116 | 369 | 372 | 4.42 | |
| 117 | 88 | 90 | 3.72 | |
| 118 | 82 | 85 | 3.86 | |
| 119 | amorphous | | 3.60 | 516 |
| 120 | 213 | 220 | 3.25 | |
| 121 | 268 | 271 | 3.58 | |
| 122 | 214 | 226 | 3.38 | |

Example 123

[3-(1-Methyl-piperidin-4-yloxymethyl)-phenyl]-[4-(3-p-tolyl-1H-pyrazol-4-yl)-pyrimidin-2-yl]-amine The title compound is prepared as described in Example 25 using 3-(1-methyl-piperidin-4-yloxymethyl)-phenylamine.

3-(1-Methyl-piperidin-4-yloxymethyl)-phenylamine is prepared as follows:

A 500 mL 4-necked flask with mechanical stirrer, N$_2$ inlet and reflux condenser is charged with 9.3 g (37.2 mmol) 1-methyl-4-(3-nitro-benzyloxy)-piperidine and 150 mL of acetic acid. Under efficient stirring 13.14 g (223 mmol) of iron powder is added and the mixture heated in an oil bath. At around 90 to 100° C. an exothermic reaction starts. The heating is interrupted for about 15 min until the exothermic reaction ceases and then the mixture is re-immersed into the oil bath and heated for 1 h at 120° C. The mixture is transferred to a round-bottomed flask and the solvent removed under reduced pressure. The residue is taken up in 1N HCl and washed with ethyl acetate (3×200 mL). The aqueous phase is treated with sodium carbonate until PH 9-10. The voluminous precipitate is removed by filtration through Celite and the solid washed extensively with ethyl acetate. The aqueous filtrate and the ethyl acetate washings are separated and the aqueous phase extracted with ethyl acetate. The organic phase is washed with brine, dried with sodium sulfate and evaporated. According to the H-NMR the residue is composed of a 1:1 mixture of the desired aniline and the corresponding acetanilide. The mixture is therefore dissolved in 50 mL of ethanol and treated with 50 mL of 2N NaOH. The resulting mixture is heated 20 h under reflux. After cooling the ethanol is distilled off and the remaining aqueous phase extracted with dichloromethane (2×150 mL). The organic phases are washed with brine, dried with potassium carbonate and evaporated. 3-(1-Methyl-piperidin-4-yloxymethyl)-phenylamine is obtained as a brown viscous oil and used without further purification. HPLC: 7.54 (System X2); [M+H]$^+$221.0.

1-Methyl-4-(3-nitro-benzyloxy)-piperidine is prepared as follows:

4-Hydroxy-1-methylpiperidine (11.5 g, 0.1 mol) is dissolved in 250 mL dichloromethane. A solution of 100 g NaOH in 100 mL of water is added followed by 17.2 g (0.1 mol) 3-nitro-benzylchloride and a catalytic amount of benzyl-triethylammonium chloride. The mixture is stirred very efficiently during 2 h at rt and then poured into 300 mL of ice-cold water. The organic layer is separated and the organic phase extracted once more with dichloromethane. The organic phase is extracted with 1N HCl (2×200 mL) and the aqueous extracts adjusted to pH 9-10 by the addition of solid sodium carbonate. The basic solution is extracted with ethyl acetate (2×200 mL) and the organic phase washed with brine, dried over potassium carbonate and evaporated. 1-Methyl-4-(3-nitro-benzyloxy)-piperidine is obtained as brown viscous oil. HPLC: 1.35 (System XS); [M+H]$^+$ 251.0.

Example 124

[3-(1-Methyl-piperidin-4-ylmethoxy)-phenyl]-[4-(3-p-tolyl-1H-pyrazol-4yl)-pyrimidin-2-yl]-amine The title compound is prepared as described in Example 1 using ethyl-4-methylbenzoate (see Example 25) and [3-(1-methyl-piperidin-4-ylmethoxy)-phenyl]-carbamic acid tert-butyl ester (see Example 27).

Example 125

[3-(1-Methyl-piperidin-4ylmethoxy)-phenyl]-[4-(1-methyl-3-p-tolyl-1H-pyrazol-4-yl)-pyrimidin-2-yl]-amine 3-(1-Methyl-piperidin-4-ylmethoxy)-phenylamine dihydrochloride (206 mg, 0.7 mmol) is suspended in 1.5 mL n-butanol and 1.5 mL dioxane. 2-Chloro-4-(1-methyl-3-p-tolyl-1H-pyrazol-4-yl)-pyrimidine (100 mg, 0.35 mmol) is added and the mixture heated under reflux for 15 h. The yellow suspension is evaporated to dryness and the residue portioned between 8 mL 20% potassium carbonate solution and 10 mL dichloromethane. The organic phase is dried with sodium sulfate and evaporated. The crude product is purified by flash-chromatography on Silica Gel using dichloromethane/methanol 100:1.25→100:5 and then dichloromethane/methanol/conc. ammonia 100:5:0.25→100:10:0.25. The title compound is obtained as a foam.

2-Chloro-4-(1-methyl-3-p-tolyl-1H-pyrazol-4-yl)-pyrimidine is prepared as follows:

2-Chloro-4-(3p-tolyl-1H-pyrazol-4-yl)-pyrimidine (see Example 25, 1.35 g, 0.005 mol) is suspended in 20 mL of toluene and treated with 2.7 mL (0.019 mol) N,N-dimeylformamide-dimethylacetal. The reaction mixture is heated 1 h at 60° C. and then 16 h at 120° C. The clear yellow solution is evaporated. The crystalline residue is triturated with 10 mL of ether. The crystalline material is collected by filtration, washed with ether and dried. 2-Chloro-4-(3-p-tolyl-1H-pyrazol-4-yl)-pyrimidine is obtained as colorless crystals. m.p. 194-197° C.; HPLC: 7.54 (System X2); [M+H]$^+$ 221.0.

3-(1-Methyl-piperidin-4-ylmethoxy)-phenylamine dihydrochloride is prepared as follows:

[3-(1-Methyl-piperidin-4-ylmethoxy)-phenyl]-carbamic acid tert-butyl ester (1.6 g, 0.005 mol) is dissolved in 10 mL of methanol and treated with 10 mL 6 N HCl. The solution is stirred at rt over night and then heated for 4 h to 60° C. The solvent is removed under reduced pressure and the residue dried under vacuum to give a tan foam which is used without further purification. HPLC: 8.20 (System X2); [M+H]$^+$ 221.0.

Example 126

4-[4-(3-p-Tolyl-1H-pyrazol-4-yl)-pyrimidin-2-ylamino]-benzenesulfonamide

The title compound is prepared as described in Example 1 using ethyl-4-methylbenzoate (see Example 25) and 4-amino-benzenesulfonamide.

| Example No. | melting point from | to | HPLC [min]/ System | mass spectra; ESI; m/z = |
|---|---|---|---|---|
| 123 | 201 | 203 | 1.50/XS | 455.0[M + H]$^+$ |
| 124 | 207 | 208 | 1.54/XS | 455.0[M + H]$^+$ |
| 125 | Foam | | 1.65/XS | 469.0[M + H]$^+$ |
| 126 | 245 | 249 | 8.82/X1 | 407.0[M + H]$^+$ |

Example 127

Dry-Filled Capsules 5000 capsules, each comprising as active ingredient 0.25 g of one of the compounds of formula I mentioned in the preceding Examples, are prepared as follows:

| | |
|---|---|
| active ingredient | 1250 g |
| talcum | 180 g |
| wheat starch | 120 g |
| magnesium stearate | 80 g |
| lactose | 20 g |

Preparation process: The mentioned substances are pulverised and forced through a sieve of 0.6 mm mesh size. 0.33 g portions of the mixture are introduced into gelatin capsules using a capsule-filling machine.

Example 128

Soft Capsules 5000 soft gelatin capsules, each comprising as active ingredient 0.05 g of one of the compounds of formula I mentioned in the preceding Examples, are prepared as follows:

| | |
|---|---|
| active ingredient | 250 g |
| PEG 400 | 1 litre |
| Tween 80 | 1 litre |

Preparation process: The active ingredient is pulverised and suspended in PEG 400 (polyethylene glycol having an M$_r$ of from approx. 380 to approx. 420, Fluka, Switzerland) and Tween®80 (polyoxyethylene sorbitan monolaurate, Atlas Chem. Ind. Inc., USA, supplied by Fluka, Switzerland) and ground in a wet pulveriser to a particle size of approx. from 1 to 3 µm. 0.43 9 portions of the mixture are then introduced into soft gelatin capsules using a capsule-filling machine.

Example 129

Inhibition of the tyrosine kinase Activity of EGF-R (HER-1), ErbB-2 (HER-2) and VEGF Receptor (KDR)

The inhibition tests are carried out as described above. The IC$_{50}$ values for some of the compounds of formula I are given below:

| Compound from Example No. | HER-1 IC$_{50}$ [µM] | HER-2 IC$_{50}$ [µM] | KDR IC$_{50}$ [µM] |
| --- | --- | --- | --- |
| 1 | 0.018 | 0.023 | 0.01 |
| 2 | 0.022 | 0.019 | 0.021 |
| 18 | 0.021 | 0.013 | 0.004 |
| 20 | 0.027 | 0.015 | 0.006 |
| 21 | 0.029 | 0.016 | 0.015 |
| 46 | 0.028 | 0.006 | 0.003 |
| 60 | 0.02 | 0.044 | 0.01 |
| 91 | 0.018 | 0.042 | 0.028 |
| 101 | 0.013 | 0.028 | 0.004 |
| 109 | 0.016 | 0.034 | 0.003 |
| 116 | 0.009 | <0.01 | 0.021 |
| 124 | 0.003 | 0.017 | 0.005 |

What is claimed is:

1. A compound of formula I

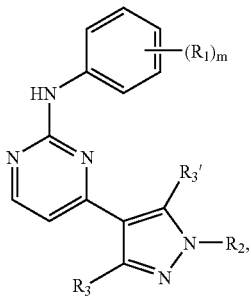

(I)

wherein m is from 1 to 3;

R$_1$ is amino-sulfonyl; N,N-di-lower alkylamino; lower alkyl-piperazinyl; lower alkyl substituted by lower alkyl-piperazinyl; a radical R$_4$-lower alkyl-X—, wherein R$_4$ is N,N-di-lower alkylamino, morpholinyl or lower alkyl-piperidyl, and X is —S— or —O—; or a radical R$_5$—C(=O)—, wherein R$_5$ is lower alkyl, hydroxyl, lower alkoxy or lower alkyl-piperazinyl; wherein the R$_1$ substituents are selected independently of one another if m>1;

R$_2$ is hydrogen;

R$_3$ is a radical of the formula Ia

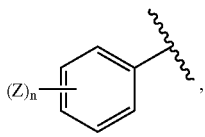

(Ia)

wherein n is 1 or 2; and

Z is chloro, lower alkyl, hydroxy, lower alkoxy, or phenyl-lower alkoxy; wherein the Z substituents are selected independently of one another if n>1; and R$_3$' is hydrogen;

or a salt of the said compounds.

2. A compound of formula I according to claim 1, wherein m is from 1 or 2;

R$_1$ is amino-sulfonyl; N,N-di-lower alkylamino; lower alkyl-piperazinyl; lower alkyl substituted by lower alkyl-piperazinyl; or a radical R$_5$—C(=O)—, wherein R$_5$ is lower alkyl, hydroxyl, lower alkoxy or lower alkyl-piperazinyl; wherein the R$_1$ substituents are selected independently of one another if m is 2;

R$_2$ is hydrogen;

R$_3$ is a radical of the formula Ia, wherein n is 1 or 2 and Z is chloro, lower alkyl, hydroxy, or lower alkoxy; wherein the Z substituents are selected independently of one another if n is 2; and R$_3$' is hydrogen;

or a salt thereof.

3. A compound of formula I according to claim 1, selected from the group consisting of {4-[3-(2,3-dimethyl-phenyl)-1H-pyrazol-4-yl]-pyrimidin-2-yl}-[4-(4-methyl-piperazin-1-yl)-phenyl]-amine;

{4-[3-(2-chloro-phenyl)-1H-pyrazol-4-yl]-pyrimidin-2-yl}-[4-(4-methyl-piperazin-1-yl)-phenyl]-amine;

4-[4-(3-p-tolyl-1H-pyrazol-4-yl)-pyrimidin-2-ylamino]-benzoic acid;

(4-Methyl-piperazin-1-yl)-{4-[4-(3-p-tolyl-1H-pyrazol-4-yl)-pyrimidin-2-ylamino]-phenyl}-methanone;

[4-(4-methyl-piperazin-1-ylmethyl)-phenyl]-[4-(3-p-tolyl-1H-pyrazol-4-yl)-pyrimidin-2-yl]-amine;

(3-{4-[3-(4-chloro-phenyl)-1H-pyrazol-4-yl]-pyrimidin-2-ylamino}-phenyl)-(4-methyl-piperazin-1-yl)-methanone;

[4-(4-ethyl-piperazin-1-ylmethyl)-phenyl]-[4-(3-p-tolyl-1H-pyrazol-4-yl)-pyrimidin-2-yl]-amine;

[3-(4-methyl-piperazin-1-ylmethyl)-phenyl]-[4-(3-p-tolyl-1H-pyrazol-4-yl)-pyrimidin-2-yl]-amine;

{4-[3-(4-chloro-phenyl)-1H-pyrazol-4-yl]-pyrimidin-2-yl}-[3-(4-methyl-piperazin-1-ylmethyl)-phenyl]-amine;

[4-(4-ethyl-piperazin-1-yl)-phenyl]-[4-(3-p-tolyl-1H-pyrazol-4-yl)-pyrimidin-2-yl]-amine;

3-{4-[3-(3,5-dimethoxy-phenyl)-1H-pyrazol-4-yl]-pyrimidin-2-ylamino}-benzenesulfonamide;

{4-[3-(4-chloro-phenyl)-1H-pyrazol-4-yl]-pyrimidin-2-yl}-[4-(4-ethyl-piperazin-1-ylmethyl)-phenyl]-amine;

{4-[3-(4-chloro-phenyl)-1H-pyrazol-4-yl]-pyrimidin-2-yl}-[4-(4-ethyl-piperazin-1-yl)-phenyl]-amine;

{4-[3-(4-chloro-phenyl)-1H-pyrazol-4-yl]-pyrimidin-2-yl}-(4-piperazin-1-yl-phenyl)-amine;

[3-(1-methyl-piperidin-4-ylmethoxy)-phenyl]-[4-(3-p-tolyl-1H-pyrazol-4-yl)-pyrimidin-2-yl]-amine;

4-[4-(3-p-tolyl-1H-pyrazol-4-yl)-pyrimidin-2-ylamino]-benzenesulfonamide and pharmaceutically acceptable salts thereof.

4. A compound of formula I according to claim 1, selected from the group consisting of {4-[3-(4-chloro-phenyl)-1H-pyrazol-4-yl]-pyrimidin-2-yl}-[4-(4-methyl-piperazin-1-yl)-phenyl]-amine;

{4-[3-(4-chloro-phenyl)-1H-pyrazol-4-yl]-pyrimidin-2-yl}-[4-(2-di methyl-amino-ethoxy)-phenyl]-amine;

{4-[3-(4-chloro-phenyl)-1H-pyrazol-4-yl]-pyrimidin-2-yl}-[4-(2-diethylamino-ethoxy)-phenyl]-amine;

{4-[3-(4-chloro-phenyl)-1H-pyrazol-4-yl]-pyrimidin-2-yl}-[4-(2-morpholin-4-yl-ethoxy)-phenyl]-amine;

{4-[3-(3-chloro-phenyl)-1H-pyrazol-4-yl]-pyrimidin-2-yl}-[4-(2-dimethylamino-ethoxy)-phenyl]-amine;

{4-[3-(3-chloro-phenyl)-1H-pyrazol-4-yl]-pyrimidin-2-yl}-[4-(2-morpholin-4-yl-ethoxy)-phenyl]-amine;

{4-[3-(3-chloro-phenyl)-1H-pyrazol-4-yl]-pyrimidin-2-yl}-[4-(2-diethylamino-ethoxy)-phenyl]-amine;

{4-[3-(3-chloro-phenyl)-1H-pyrazol-4-yl]-pyrimidin-2-yl}-[4-(4-methyl-piperazin-1-yl)-phenyl]-amine;

{4-[3-(4-methoxy-phenyl)-1H-pyrazol-4-yl]-pyrimidin-2-yl}-[4-(4-methyl-piperazin-1-yl)-phenyl]-amine;

{4-[3-(4-methoxy-phenyl)-1H-pyrazol-4-yl]-pyrimidin-2-yl}-[4-(2-morpholin-4-yl-ethoxy)-phenyl]-amine;
{4-[3-(4-ethyl-phenyl)-1H-pyrazol-4-yl]-pyrimidin-2-yl}-[4-(4-methyl-piperazin-1-yl)-phenyl]-amine;
[4-(2-diethylamino-ethoxy)-phenyl]-{4-[3-(4-ethyl-phenyl)-1H-pyrazol-4-yl]-pyrimidin-2-yl}-amine;
[4-(2-diethylamino-ethoxy)-phenyl]-{4-[3-(4-methoxy-phenyl)-1H-pyrazol-4-yl]-pyrimidin-2-yl}-amine;
[4-(2-diethylamino-ethoxy)-phenyl]-{4-[3-(3-methoxy-phenyl)-1H-pyrazol-4-yl]-pyrimidin-2-yl}-amine;
{4-[3-(3-methoxy-phenyl)-1H-pyrazol-4-yl]-pyrimidin-2-yl}-[4-(2-morpholin-4-yl-ethoxy)-phenyl]-amine;
{4-[3-(3-methoxy-phenyl)-1H-pyrazol-4-yl]-pyrimidin-2-yl}-[4-(4-methyl-piperazin-1-yl)-phenyl]-amine;
[4-(2-dimethylamino-ethoxy)-phenyl]-{4-[3-(4-ethyl-phenyl)-1H-pyrazol-4-yl]-pyrimidin-2-yl}-amine;
[4-(4-methyl-piperazin-1-yl)-phenyl]-[4-(3-m-tolyl-1H-pyrazol-4-yl)-pyrimidin-2-yl]-amine;
[4-(2-diethylamino-ethoxy)-phenyl]-[4-(3-m-tolyl-1H-pyrazol-4-yl)-pyrimidin-2-yl]-amine;
[4-(2-dimethylamino-ethoxy)-phenyl]-[4-(3-m-tolyl-1H-pyrazol-4-yl)-pyrimidin-2-yl]-amine;
{4-[3-(3,4-dichloro-phenyl)-1H-pyrazol-4-yl]-pyrimidin-2-yl}-[4-(2-dimethylamino-ethoxy)-phenyl]-amine;
{4-[3-(3,4-dichloro-phenyl)-1H-pyrazol-4-yl]-pyrimidin-2-yl}-[4-(4-methyl-piperazin-1-yl)-phenyl]-amine;
{4-[3-(4-benzyloxy-phenyl)-1H-pyrazol-4-yl]-pyrimidin-2-yl}-[4-(2-diethylamino-ethoxy)-phenyl]-amine;
4-(4-{2-[4-(4-methyl-piperazin-1-yl)-phenylamino]pyrimidin-4-yl}-1H-pyrazol-3-yl)-phenol;
[4-(4-methyl-piperazin-1-yl)-phenyl]-[4-(3-p-tolyl-1H-pyrazol-4-yl)-pyrimidin-2-yl]-amine;
[4-(2-dimethylamino-ethoxy)-phenyl]-[4-(3-p-tolyl-1H-pyrazol-4-yl)-pyrimidin-2-yl]-amine;
{4-[3-(4-chloro-phenyl)-1H-pyrazol-4-yl]-pyrimidin-2-yl}-[3-(1-methyl-piperidin-4-ylmethoxy)-phenyl]-amine;
{4-[3-(4-chloro-phenyl)-1H-pyrazol-4-yl]-pyrimidin-2-yl}-[4-(1-methyl-piperidin-4-ylmethoxy)-phenyl]-amine;
{4-[3-(4-chloro-phenyl)-1H-pyrazol-4-yl]-pyrimidin-2-yl}-[3-(4-methyl-piperazin-1-yl)-phenyl]-amine;
4-{4-[3-(4-chloro-phenyl)-1H-pyrazol-4-yl]-pyrimidin-2-ylamino}-benzoic acid;
(4-{4-[3-(4-chloro-phenyl)-1H-pyrazol-4-yl]-pyrimidin-2-ylamino}-phenyl)-(4-methyl-piperazin-1-yl)-methanone;
{4-[3-(4-chloro-phenyl)-1H-pyrazol-4-yl]-pyrimidin-2-yl}-[4-(4-methyl-piperazin-1-ylmethyl)-phenyl]-amine,
{4-[3-(2,4-dichloro-phenyl)-1H-pyrazol-4-yl]-pyrimidin-2-yl}-[4-(4-methyl-piperazin-1-yl)-phenyl]-amine;
N-{4-[3-(4-chloro-phenyl)-1H-pyrazol-4-yl]-pyrimidin-2-yl}-N',N'-dimethyl-benzene-1,3-diamine;
{4-[3-(4-ethoxy-phenyl)-1H-pyrazol-4-yl]-pyrimidin-2-yl}-[4-(4-methyl-piperazin-1-yl)-phenyl]-amine;
3-{4-[3-(4-chloro-3-hydroxy-phenyl)-1H-pyrazol-4-yl]-pyrimidin-2-ylamino}-benzenesulfonamide;
3-{4-[3-(4-chloro-3-methoxy-phenyl)-1H-pyrazol-4-yl]-pyrimidin-2-ylamino}-benzenesulfonamide;
3-{4-[3-(4-chloro-3-methoxy-phenyl)-1H-pyrazol-4-yl]-pyrimidin-2-ylamino}-benzoic acid ethyl ester;
3-{4-[3-(4-chloro-3-hydroxy-phenyl)-1H-pyrazol-4-yl]-pyrimidin-2-ylamino}-benzoic acid ethyl ester;
1-(3-{4-[3-(4-chloro-3-methoxy-phenyl)-1H-pyrazol-4-yl]-pyrimidin-2-ylamino}-phenyl)-ethanone;
benzothiazol-6-yl-{4-[3-(4-chloro-3-methoxy-phenyl)-1H-pyrazol-4-yl]-pyrimidin-2-yl}-amine;
{4-[3-(4-chloro-3-methoxy-phenyl)-1H-pyrazol-4-yl]-pyrimidin-2-yl}-(1-oxo-benzothiazol-6-yl)-amine;
3-[4-(3-benzo[1,3]dioxol-5-yl-1H-pyrazol-4-yl)-pyrimidin-2-ylamino]-benzoic acid tert-butyl ester;
3-[4-(3-benzo[1,3]dioxol-5-yl-1H-pyrazol-4-yl)-pyrimidin-2-ylamino]-benzenesulfonamide;
and pharmaceutically acceptable salts thereof.

5. A pharmaceutical composition comprising a compound of formula I or a pharmaceutically acceptable salt thereof according to claim 1, together with at least one pharmaceutically acceptable carrier.

6. A process for the preparation of a compound of formula I according to claim 1 or of a salt of such a compound, characterized in that
a) a compound of formula II

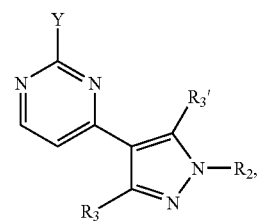

(II)

wherein Y is a leaving group such as halogen, —S(═O)—CH$_3$ or —S(O$_2$)—CH$_3$ and R$_2$, R$_3$ and R$_3$' have the meanings as defined for a compound of formula I according to claim 1, is reacted with a compound of formula III

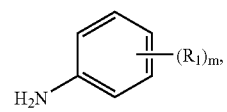

(III)

wherein m and R$_1$ have the meanings as defined for a compound of formula I according to claim 1;
b) in order to prepare a compound of formula I, wherein R$_1$ is a radical R$_5$—C(═O)— in which R$_6$ is mono- or di-substituted amino or a heterocyclic radical that is bound to the carbonyl moiety via a nitrogen ring atom, a compound of formula IV

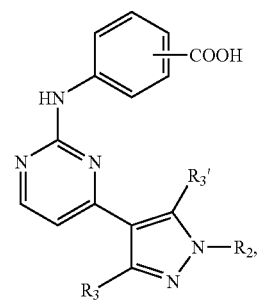

(IV)

wherein R$_2$, R$_3$ and R$_3$' have the meanings as defined for a compound of formula I according to claim 1, or a reactive carboxylic acid derivative thereof, is reacted with a mono- or di-substituted amine or a heterocyclic radical containing at least one nitrogen ring atom to which a hydrogen is bound, respectively; or c) in order to prepare a compound of formula I, wherein $R_2$ is unsubstituted or substituted lower alkyl or a heterocyclic radical, a compound of formula I, wherein $R_2$ is hydrogen, is reacted with a compound of the formula $R_2$—OH, wherein $R_2$ is unsubstituted or substituted lower alkyl or a heterocyclic radical wherein the substituted lower alkyl or the heterocyclic radical is attached to the hydroxy group of $R_2$—OH via a carbon atom of the lower alkyl moiety or via a carbon ring atom of the heterocyclic radical, respectively;

whereby functional groups which are present in the starting compounds of processes a) to c) and are not intended to take part in the reaction, are present in protected form if necessary, and protecting groups that are present are cleaved, whereby the said starting compounds may also exist in the form of salts provided that a salt-forming group is present and a reaction in salt form is possible;

and, if so desired, a compound of formula I thus obtained is converted into another compound of formula I, a free compound of formula I is converted into a salt, an obtained salt of a compound of formula I is converted into the free compound or another salt, and/or a mixture of isomeric compounds of formula I is separated into the individual isomers.

* * * * *